United States Patent
Barish et al.

(10) Patent No.: US 11,439,635 B2
(45) Date of Patent: Sep. 13, 2022

(54) B CELL LYMPHOMA 6 PROTEIN (BCL6) AS A TARGET FOR TREATING DIABETES MELLITUS AND NON-ALCOHOLIC FATTY LIVER DISEASE

(71) Applicant: NORTHWESTERN UNIVERSITY, Evanston, IL (US)

(72) Inventors: Grant D. Barish, Chicago, IL (US); Meredith A. Sommars, Winfield, IL (US); Madhavi D. Senagolage, Cicero, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 43 days.

(21) Appl. No.: 16/943,519

(22) Filed: Jul. 30, 2020

(65) Prior Publication Data

US 2021/0030740 A1 Feb. 4, 2021

Related U.S. Application Data

(60) Provisional application No. 62/880,371, filed on Jul. 30, 2019.

(51) Int. Cl.
*A61K 31/4725* (2006.01)
*A61K 31/427* (2006.01)
*A61K 31/506* (2006.01)
*A61K 9/00* (2006.01)

(52) U.S. Cl.
CPC ........ *A61K 31/4725* (2013.01); *A61K 31/427* (2013.01); *A61K 31/506* (2013.01); *A61K 9/0053* (2013.01)

(58) Field of Classification Search
None
See application file for complete search history.

(56) References Cited

PUBLICATIONS

American Diabetes Association. Economic Costs of Diabetes in the U.S. in 2017. Diabetes Care. 2018;41(5):917-28.
Barish GD, et al. Bcl-6 and NF-kappaB cistromes mediate opposing regulation of the innate immune response. Genes Dev. 2010;24(24):2760-5.
Brunt EM, et al. Nonalcoholic steatohepatitis: a proposal for grading and staging the histological lesions. Am J Gastroenterol. 1999;94(9):2467-74.
Cardenas et al., "Rationally designed BCL6 inhibitors target activated B cell diffuse large B cell lymphoma," J. Clin. Invest. 2016;126(9): 3351-3362.
Cerchietti et al., "A small molecule inhibitor of BCL6 kills DLBCL cells in vitro and in vivo," Cancer Cell. Apr. 13, 2010; 17(4):400-411.
Chiang, J.Y.L. et al. Bile acid receptors FXR and TGR5 signaling in fatty liver diseases and therapy. Am J Physiol Gastrointest Liver Physiol, 2020. 318(3): p. G554-G573.
Dent AL, et al. Control of inflammation, cytokine expression, and germinal center formation by BCL-6. Science. 1997;276(5312):589-92.
Dyson JK, et al. Non-alcoholic fatty liver disease: a practical approach to treatment. Frontline Gastroenterol. 2014;5(4):277-86.
Ekstedt M, et al. Long term follow-up of patients with NAFLD and elevated liver enzymes. Hepatology. 2006;44(4):865-73.
Farrell G, et al. Mouse Models of Nonalcoholic Steatohepatitis: Toward Optimization of Their Relevance to Human Nonalcoholic Steatohepatitis. Hepatology. 2019;69(5):2241-57.
Grindberg RV, et al. "RNA-sequencing from single nuclei." Proceedings of the National Academy of Sciences 110.49 (2013): 19802-19807.
Hetal, T. et al. "A review on techniques for oral bioavailability enhancement of drugs." Health 4.3 (2010): 033.
Kerres, N., et al. "Chemically induced degradation of the oncogenic transcription factor BCL6." Cell Reports 20.12 (2017): 2860-2875.
Kleiner DE, et al. Nonalcoholic Steatohepatitis Clinical Research N. Design and validation of a histological scoring system for nonalcoholic fatty liver disease. Hepatology. 2005;41(6):1313-21.
Lapensee, C. R., et al. "Deficiency of the transcriptional repressor B cell lymphoma 6 (Bcl6) is accompanied by dysregulated lipid metabolism." PLoS One 9.6 (2014): e97090.
Liang W, et al. Establishment of a general NAFLD scoring system for rodent models and comparison to human liver pathology. PloS one. 2014;9(12):e115922.
Lu et al., "PRMT5 interacts with the BCL6 oncoprotein and is required for germinal center formation and lymphoma cell survival," Blood, 2018;132(19):2026-2039.
Matteoni CA, et al. Nonalcoholic fatty liver disease: a spectrum of clinical and pathological severity. Gastroenterology. 1999;116(6):1413-9.
Opnme. Collaborate now with our scientists to pursue your novel disease hypothesis for our oral BCL6 degrader. Apr. 15, 2019. Accessed online at Https://opnme.com/molecules/oral-bcl6-degrader-news.
Ozcan, U., et al., Chemical chaperones reduce ER stress and restore glucose homeostasis in a mouse model of type 2 diabetes. Science, 2006. 313(5790): p. 1137-40.
Peterson RG, et al. Glucose dysregulation and response to common anti-diabetic agents in the FATZO/Pco mouse. PloS one. 2017;12(6):e0179856.
Roglic G, World Health Organization. Global report on diabetes. Geneva, Switzerland: World Health Organization; 2016. 88 pages.
Senagolage, M. D., et al. "Loss of transcriptional repression by BCL6 confers insulin sensitivity in the setting of obesity." Cell reports 25.12 (2018): 3283-3298.
Sommars MA, et al. Dynamic repression by BCL6 controls the genome-wide liver response to fasting and steatosis. Elife. 2019;8.
Sun G, et al. The FATZO mouse, a next generation model of type 2 diabetes, develops NAFLD and NASH when fed a Western diet supplemented with fructose. BMC Gastroenterol. 2019;19(1):41.

(Continued)

*Primary Examiner* — Heidi Reese
(74) *Attorney, Agent, or Firm* — Quarles & Brady LLP

(57) ABSTRACT

Disclosed are methods and compositions for treating diabetes mellitus and non-alcoholic fatty liver disease by administering a therapeutic agent that inhibits the biological activity of B cell lymphoma 6 protein (BCL6).

8 Claims, 39 Drawing Sheets

(56) References Cited

PUBLICATIONS

Thomas, C., et al., TGR5-mediated bile acid sensing controls glucose homeostasis. Cell Metab, 2009. 10(3): p. 167-77.

Watanabe, M., et al., Bile acids induce energy expenditure by promoting intracellular thyroid hormone activation. Nature, 2006. 439(7075): p. 484-9.

Watanabe, M., et al., Bile acids lower triglyceride levels via a pathway involving FXR, SHP, and SREBP-1c. J Clin Invest, 2004. 113(10): p. 1408-18.

Younossi ZM, et al. The economic and clinical burden of nonalcoholic fatty liver disease in the United States and Europe. Hepatology. 2016;64(5):1577-86.

| Name | P-value | Motif |
|---|---|---|
| HNF6 | 1x10⁻⁵⁷⁰ | aTATtGATCt |
| FOXA1 | 1x10⁻⁵⁶⁰ | AAGTAAACA |
| BCL6 | 1x10⁻⁴⁵⁰ | TCCTAGAAAC |
| CEBP | 1x10⁻³⁹⁰ | ATTcCCAAC |
| HNF4g | 1x10⁻³⁵⁰ | CAAAGTtCAAAGTtCA |
| PPAR | 1x10⁻³⁵⁰ | TGACCTTtgCCCA |

US 11,439,635 B2

B CELL LYMPHOMA 6 PROTEIN (BCL6) AS A TARGET FOR TREATING DIABETES MELLITUS AND NON-ALCOHOLIC FATTY LIVER DISEASE

CROSS-REFERENCE TO RELATED PATENT APPLICATIONS

The present application claims the benefit of priority under 35 U.S.C. 119(e) to U.S. Provisional Application No. 62/880,371, filed on Jul. 30, 2019, the content of which is incorporated herein by reference in its entirety.

STATEMENT REGARDING FEDERALLY SPONSORED RESEARCH OR DEVELOPMENT

This invention was made with government support under DK108987, HL092298, GM008061, and DK020595 awarded by the National Institutes of Health. The government has certain rights in the invention.

BACKGROUND

The invention relates to methods and compositions for treating diabetes mellitus and non-alcoholic fatty liver disease. In particular, the intention relates to methods for treating diabetes mellitus and non-alcoholic fatty liver disease by administering a therapeutic agent that inhibits the biological activity of B cell lymphoma 6 protein (BCL6).

B cell lymphoma protein 6 (BCL6) is a transcription factor that promotes oncogenesis in lymphoid malignancies such as diffuse large B cell lymphoma. (See Kerres et al., 2017, Cell Reports 20, 2860-2875; the content of which is incorporated herein by reference in its entirety). In particular, BCL6 represses genes whose expression would otherwise prevent the proliferation and survival of B cells by recruiting the SMRT, NCOR, and BCOR corepressors to BCL6's N-terminal BTB domain. (See Cardenas et al., "Rationally designed BCL6 inhibitors target activated B cell diffuse large B cell lymphoma," J. Clin. Invest. 2016; 126(9): 3351-3362; and Cerchietti et al., "A small molecule inhibitor of BCL6 kills DLBCL cells in vitro and in vivo," Cancer Cell. 2010 Apr. 13; 17(4):400-411; the contents of which are incorporated herein by reference in their entireties). The binding site for these corepressors consists of an extended groove formed through obligate homodimerization of BCL6 BTB. (See id.). The biological activity of BCL6 also is regulated by methylation. (See Lu et al., "PRMT5 interacts with the BCL6 oncoprotein and is required for germinal center formation and lymphoma cell survival," Blood, 2018; 132(19):2026-2039; the content of which is incorporated herein by referenced in its entirety.)

Here, using various in vitro and in vivo mouse models the inventors have shown that BCL6 expression is involved in diabetes mellitus and non-alcoholic fatty liver disease. The inventors' results suggest that diabetes mellitus and non-alcoholic fatty liver disease can be treated by modulating BCL6 expression or biological activity.

SUMMARY

Disclosed are methods and compositions for treating diabetes mellitus and non-alcoholic fatty liver disease. In particular, the intention relates to methods for treating diabetes mellitus and non-alcoholic fatty liver disease by administering a therapeutic agent that inhibits the biological activity of B cell lymphoma 6 protein (BCL6).

DETAILED DESCRIPTION

Figure 1:
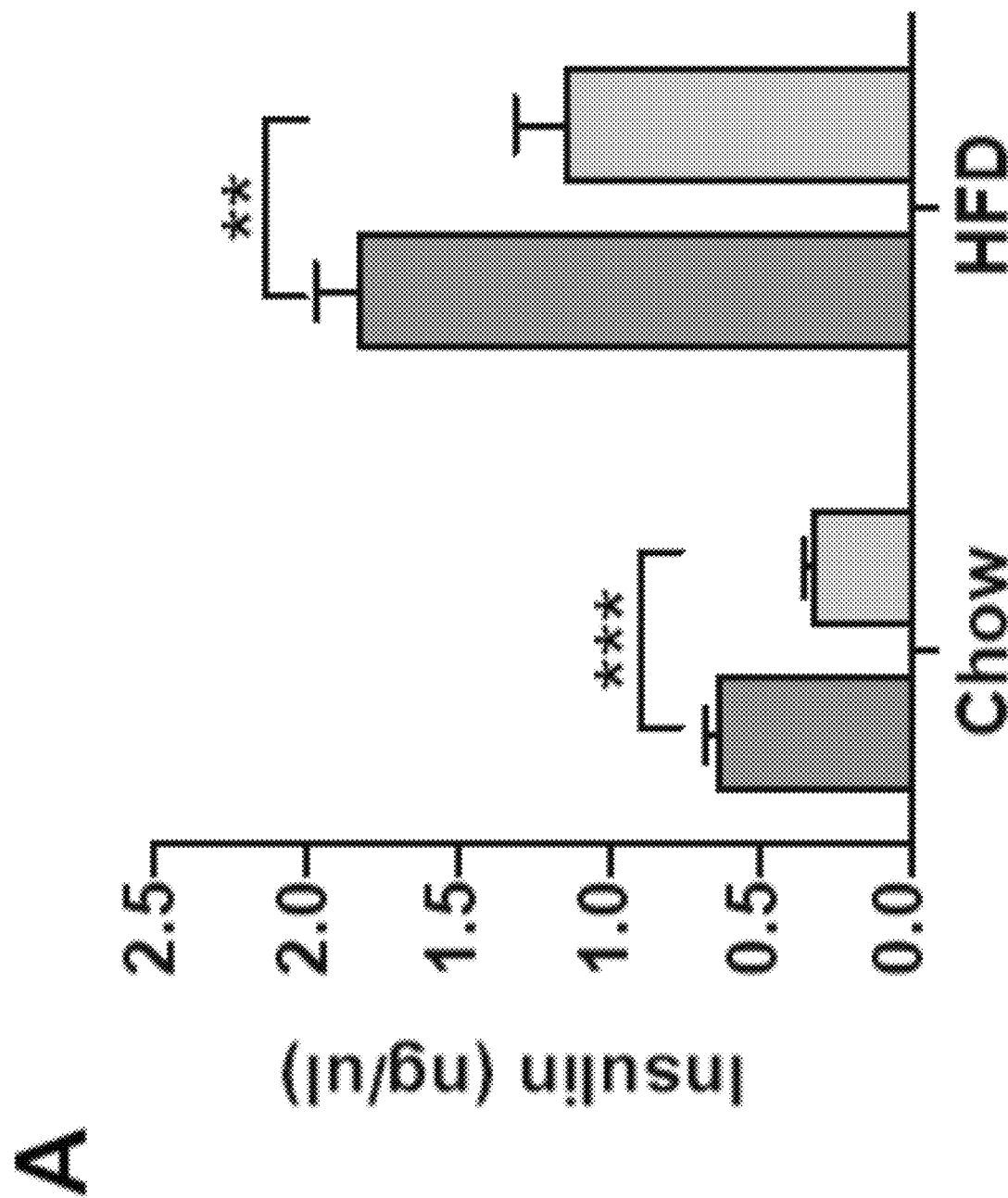
FIG. 1. Ablation of Bcl6 in adipocytes promotes insulin sensitivity and prevents steatosis. (A-B) Fasting serum insulin (A) and blood glucose levels (B) in chow or high fat diet (HFD)-fed Bcl6$^{fl/fl}$ (control) and Bcl6$^{AKO}$ (Bcl6 adipocyte-specific knockout) mice. N=9-11 per group. (C) Calculated insulin resistance based on Homeostasis Model Assessment-2 for chow and high fat diet-fed Bcl6$^{fl/fl}$ and Bcl6$^{AKO}$ mice. N=9-11 per group. (D) Glucose infusion rates over the course of hyperinsulinemic-euglycemic clamps in Bcl6$^{fl/fl}$ and Bcl6$^{AKO}$ mice performed after 8 weeks of high fat diet. N=9 per group. (E) Endogenous glucose production plotted over the course of clamping in Bcl6$^{fl/fl}$ and Bcl6$^{AKO}$ mice. N=9 per group. (F) Total glucose flux (Rd) before and during insulin clamps of Bcl6$^{fl/fl}$ and Bcl6$^{AKO}$ mice. N=9 per group. (G) Tissue-specific glucose uptake in Bcl6$^{fl/fl}$ and Bcl6$^{AKO}$ mice under clamp conditions. N=9 per group. (H) Liver triglyceride content (mg of triglyceride/g of tissue) in chow and high fat diet (HFD)-fed Bcl6$^{fl/fl}$ and Bcl6$^{AKO}$ mice. N=7-9 per group. (I) Hematoxylin and eosin staining of representative livers from Bcl6$^{fl/fl}$ and Bcl6$^{AKO}$ mice after 12 weeks of high fat diet.
Figure 1:
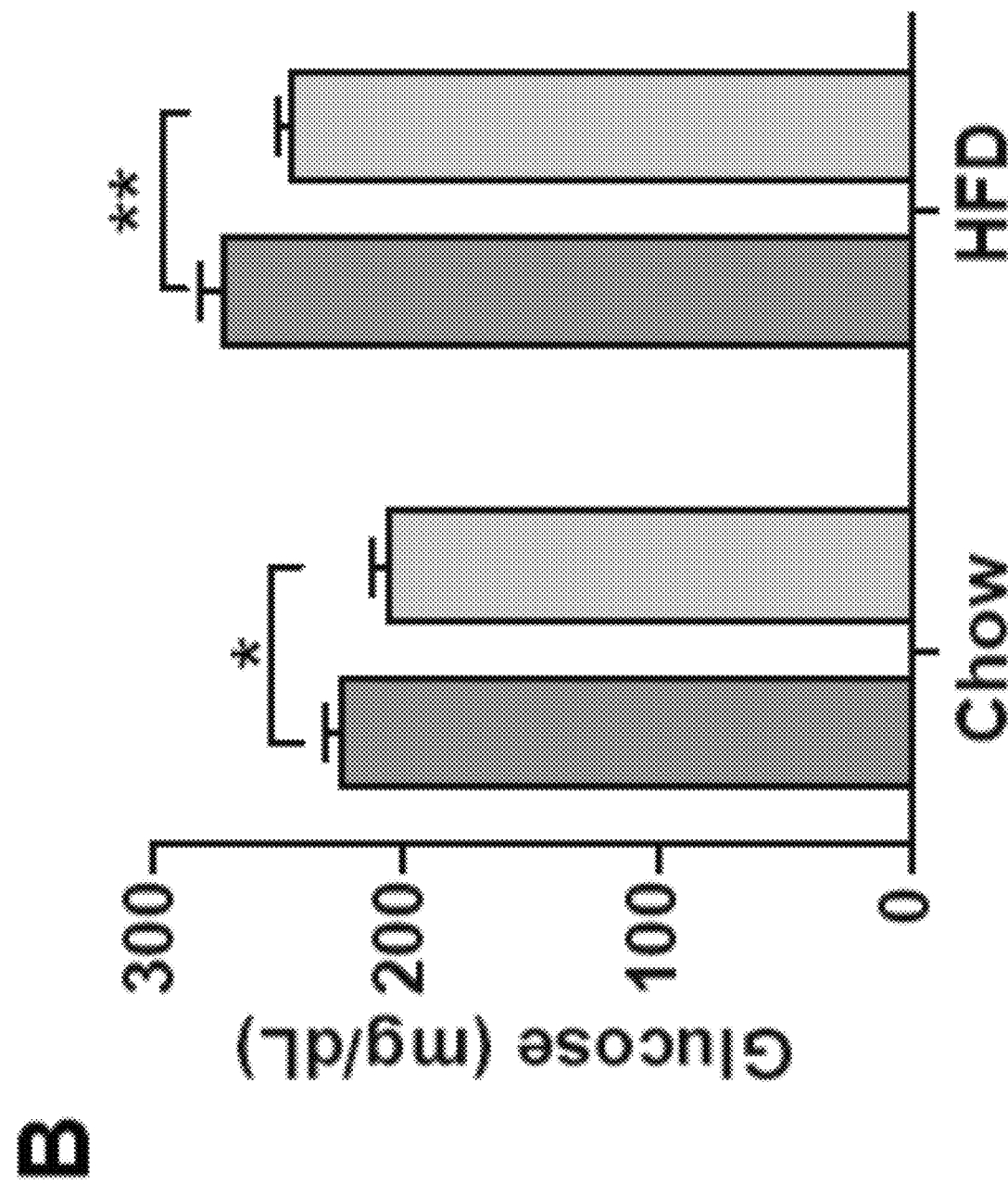
Figure 1:
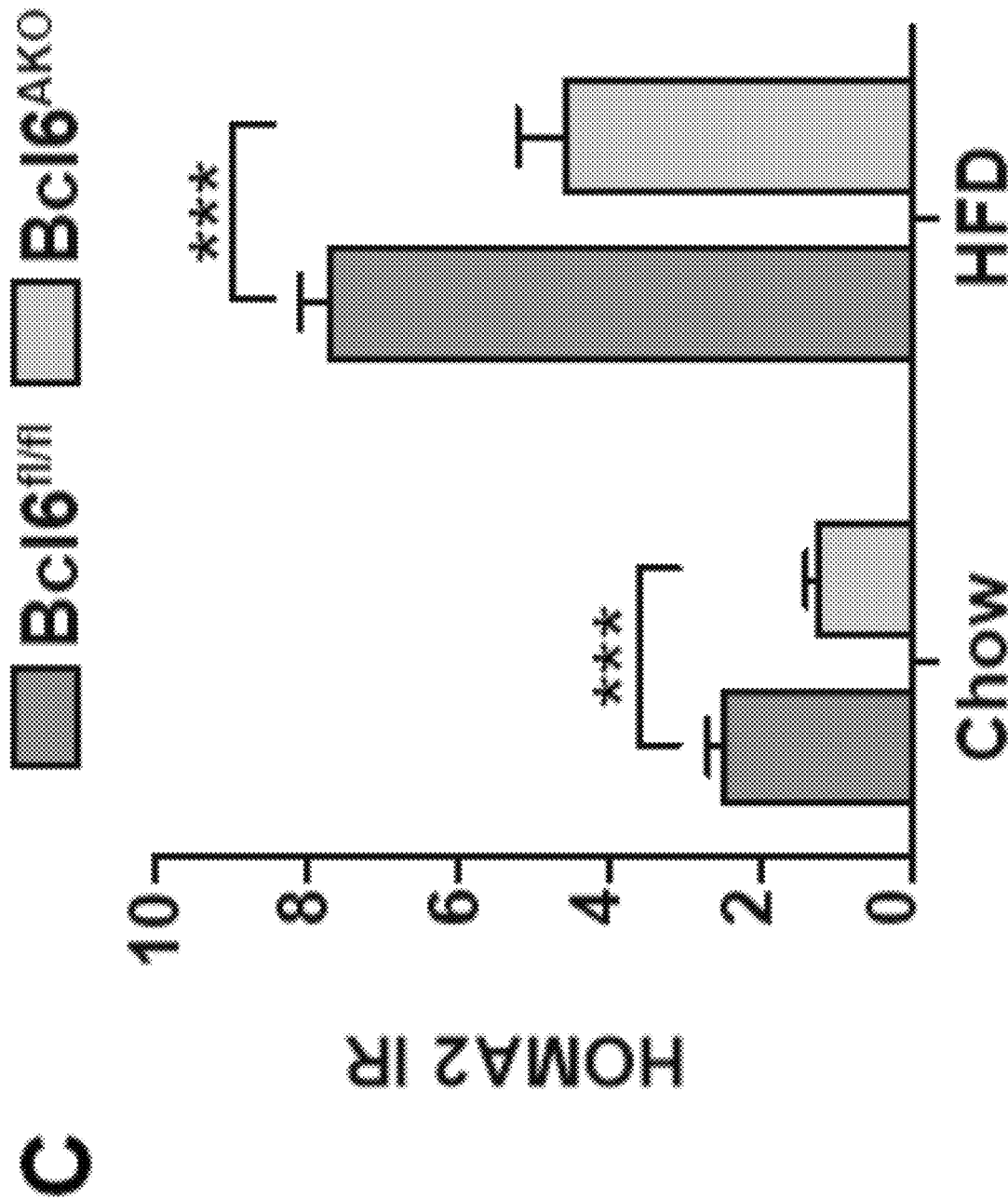
Figure 1:
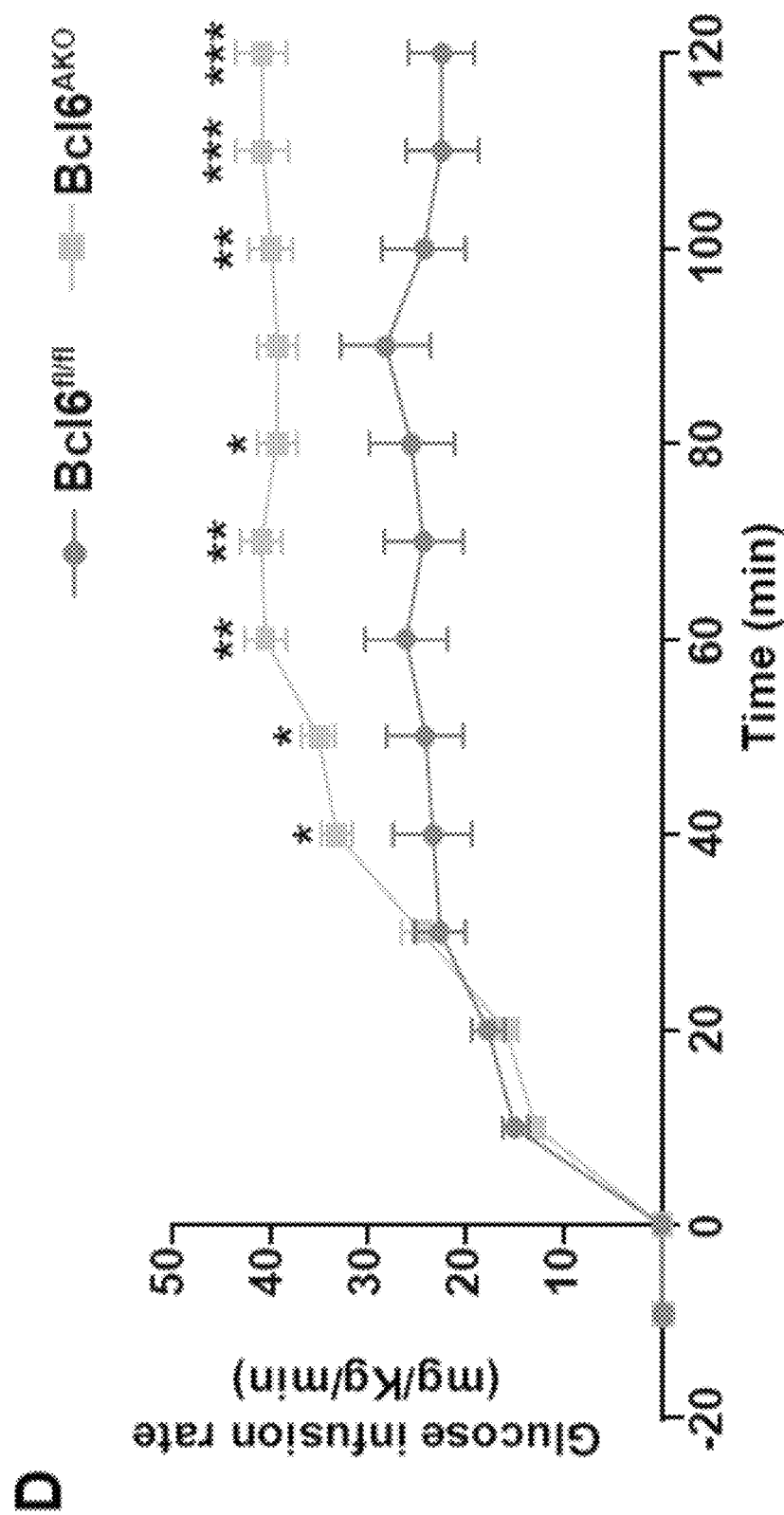
Figure 1:
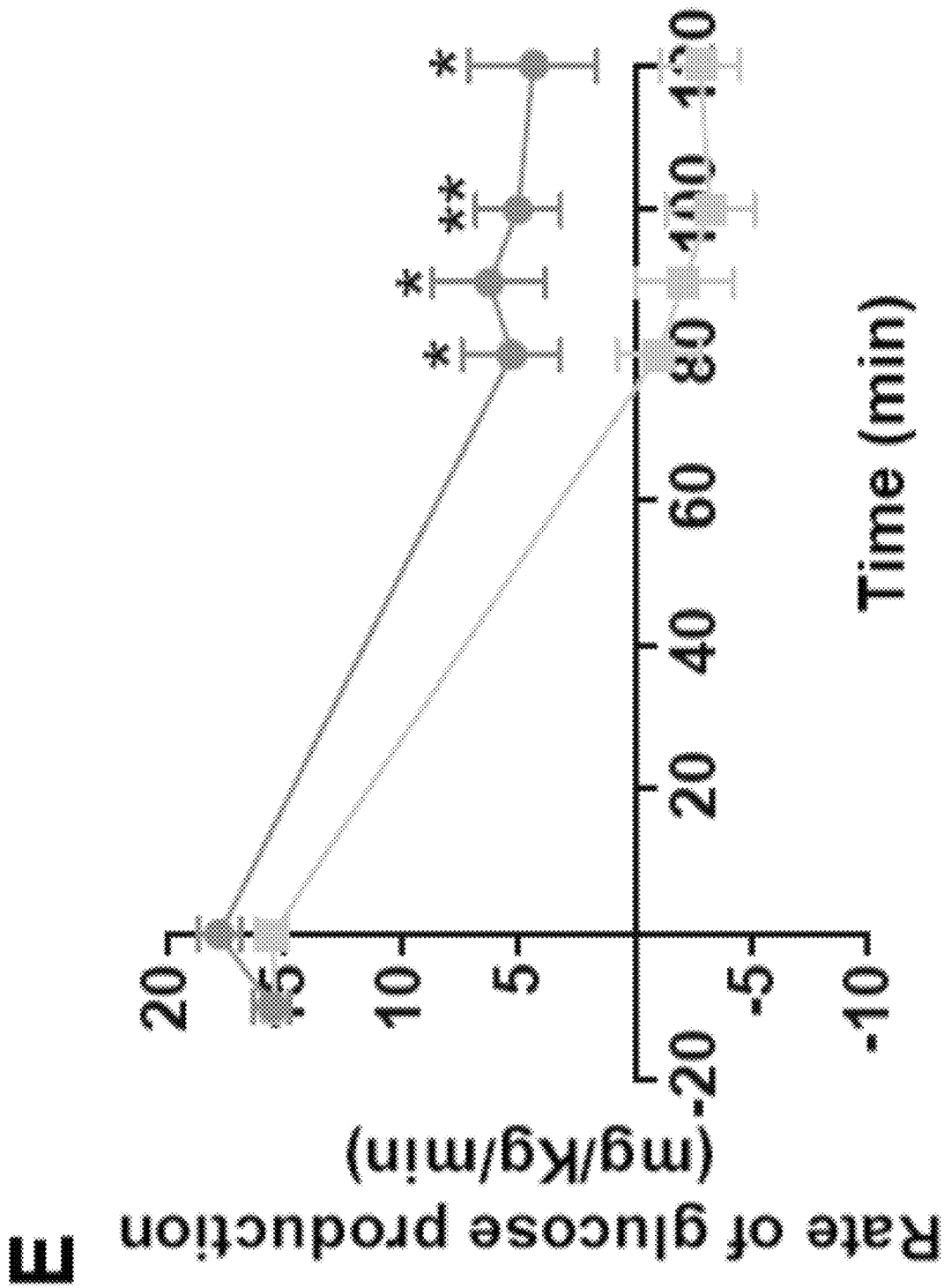
Figure 1:
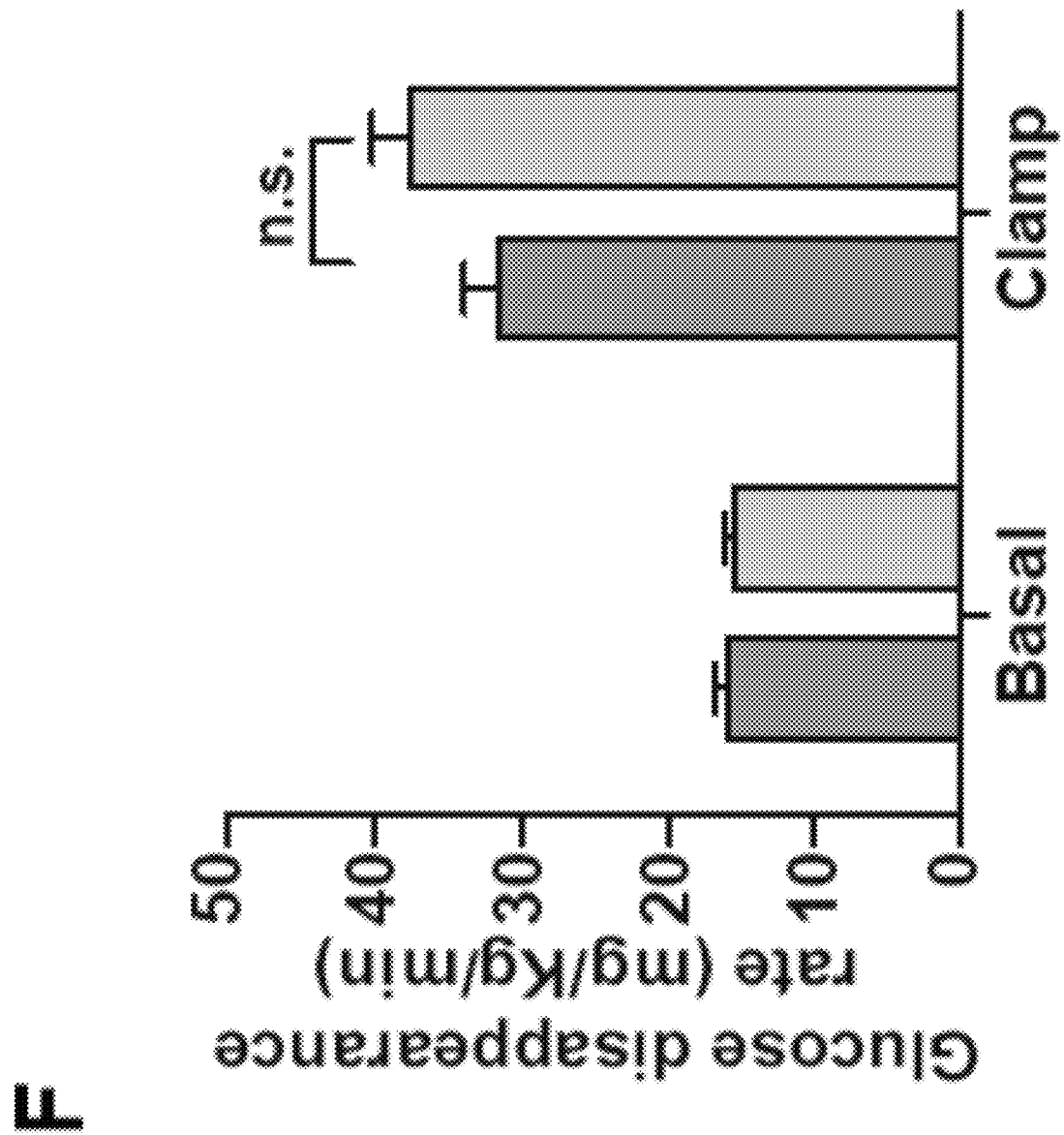
Figure 1:
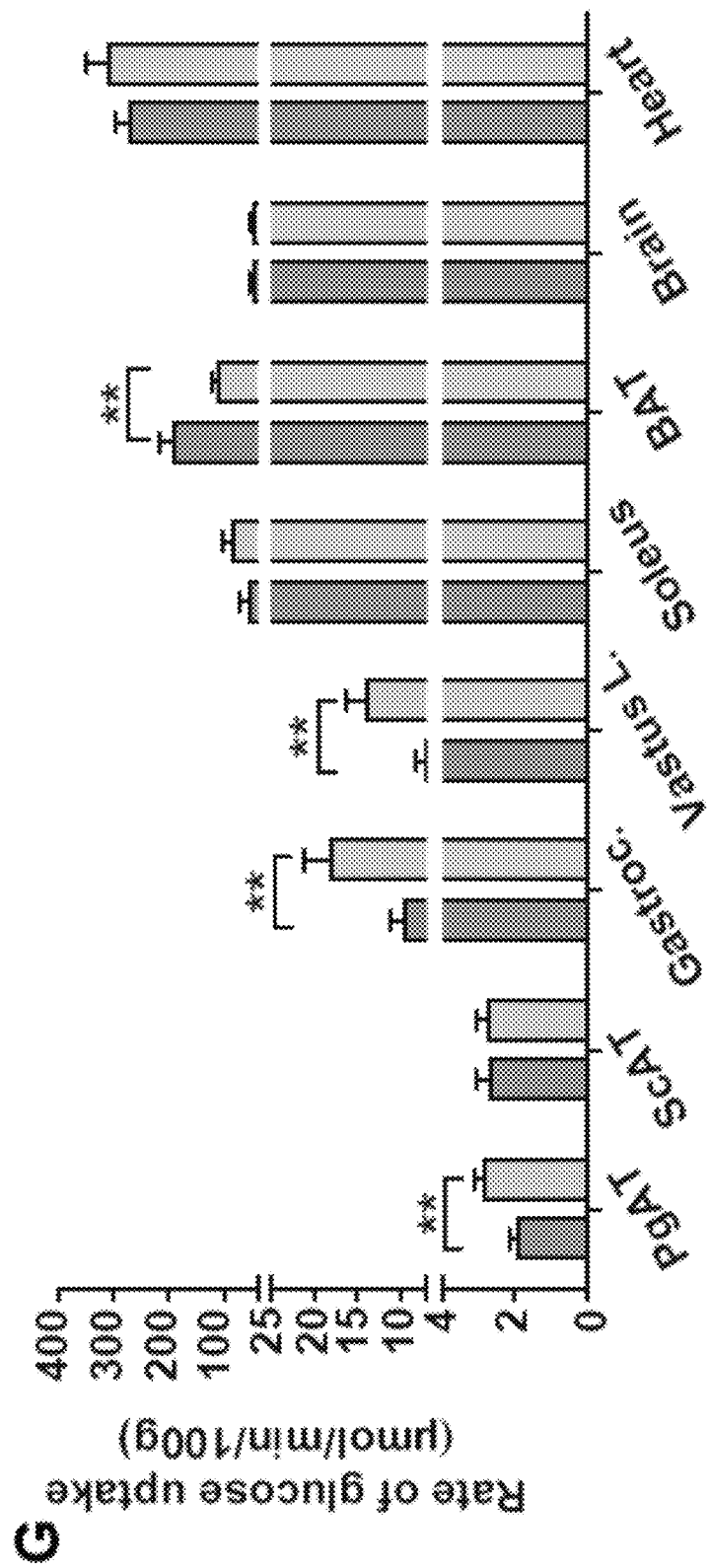
Figure 1:
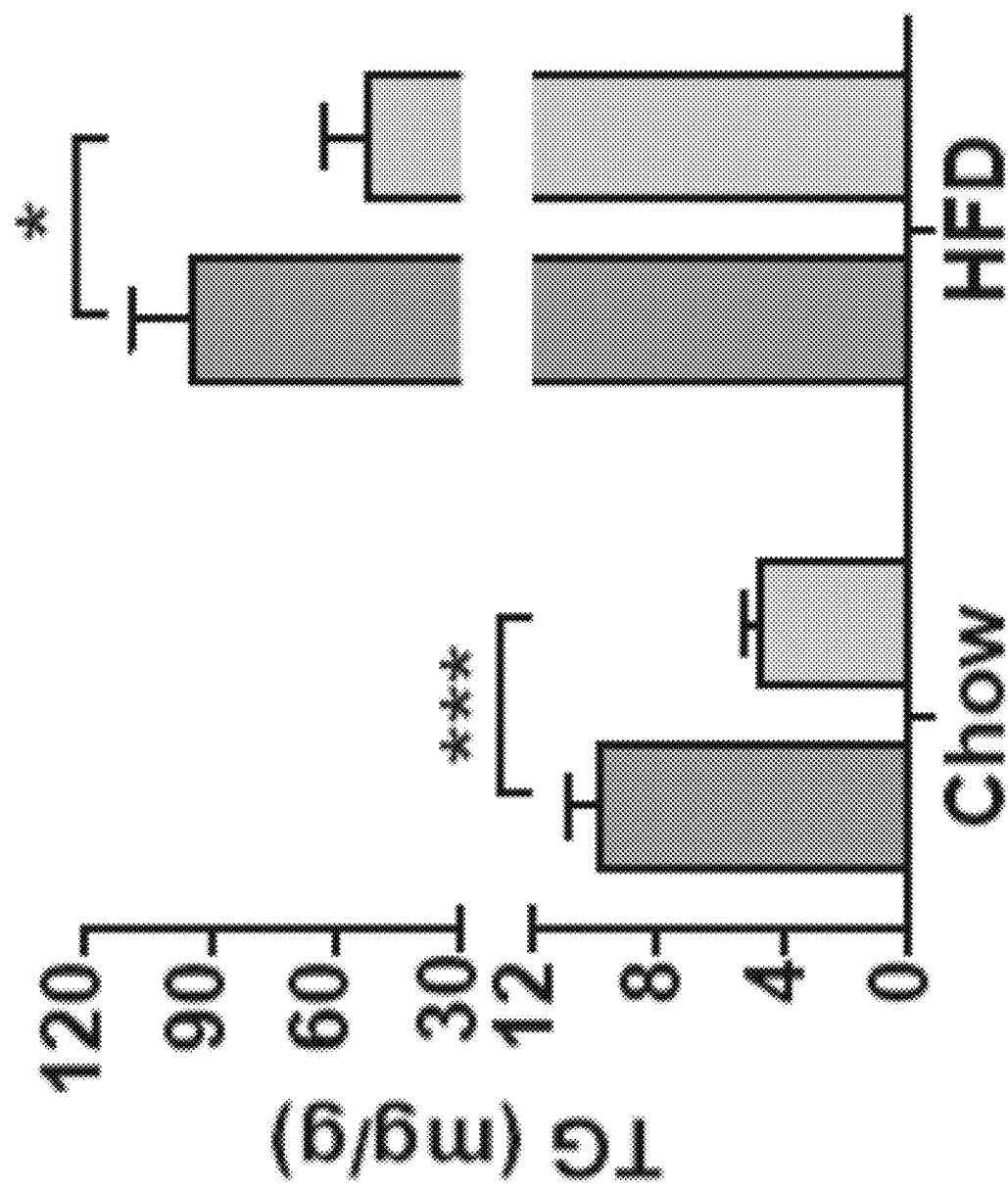
Figure 1:
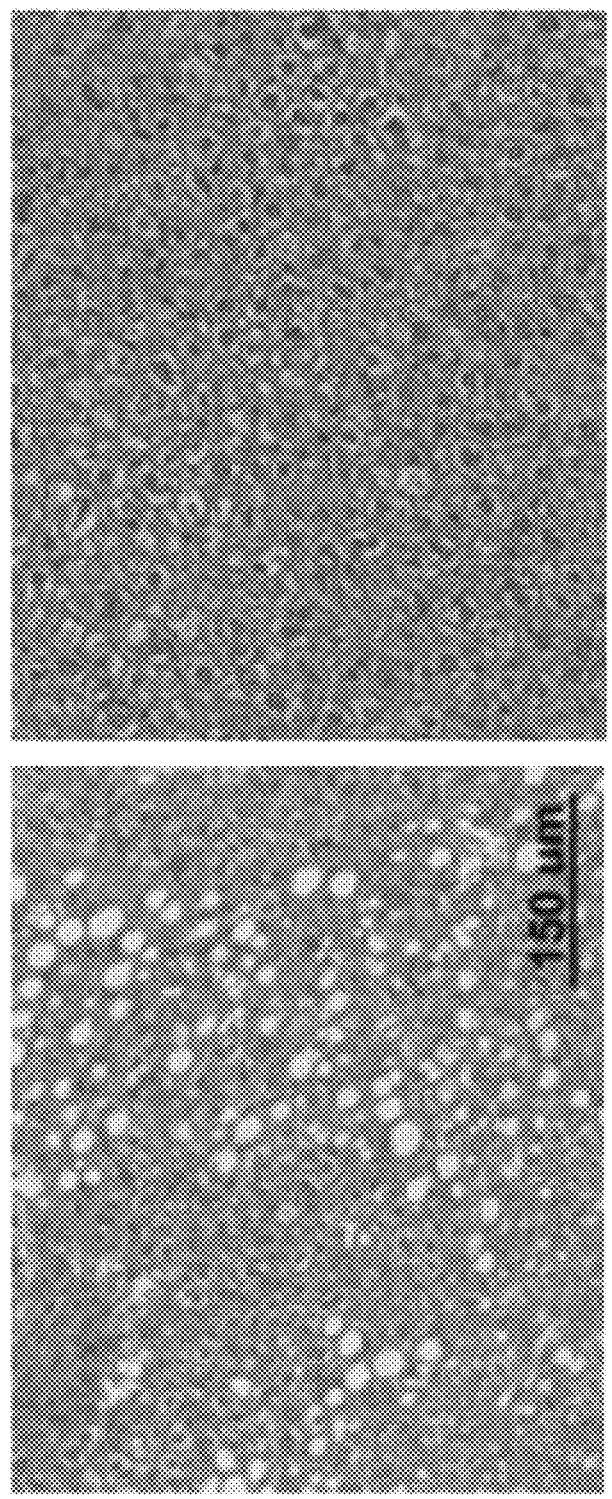

Disclosed are methods and compositions for treating diabetes mellitus and non-alcoholic fatty liver disease. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient.

As used herein, the term "subject" is meant to encompass a person who has diabetes mellitus or is at risk for developing diabetes mellitus, for example diabetes mellitus type 2. The term "subject" also is meant to encompass a person having or at risk for developing non-alcoholic fatty liver disease. The term "subject" also is meant to encompass a person who has diabetes mellitus or is at risk for developing diabetes mellitus, for example diabetes mellitus type 2, and who has or is at risk for developing non-alcoholic fatty liver disease.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

The disclosed methods and compositions relate to treating and/or preventing diseases and disorders such as diabetes mellitus and/or non-alcoholic fatty liver disease by administering a therapeutic agent that inhibits the biological activity of B cell lymphoma protein 6 (BCL6).

The methods disclosed herein typically include a step of administering a therapeutic agent that inhibits the biological activity of B cell lymphoma protein 6 (BCL6). As used herein, the term "inhibit" means decreasing or inhibiting activity, for example inhibiting biological activity of BCL6. The therapeutic agents utilized in the disclosed methods may inhibit the biological activity of BCL6 directly and/or indirectly by interacting with BCL6 directly and/or indirectly. In some embodiments, the therapeutic agents induce the degradation of BCL6. In other embodiments, the therapeutic agents disrupt formation of a BCL6 repression complex. In some embodiments, the therapeutic agent binds to BCL6, optionally at its corepressor binding groove of its BTB domain. In other embodiments, the therapeutic agents inhibit methylation of BCL6, optionally by inhibiting a methylase enzyme that methylates BCL6.

The therapeutic agent utilized in the treatment methods disclosed herein may exhibit one or more biological activities. The disclosed compounds may function to inhibit the biological activity of BCL6. In some embodiments, the disclosed compounds inhibit the biological activity of BCL6 by at least 50%, 60%, 70%, 80%, 90%, 95%, 96%, 97%, 98%, or 99% relative to a control at a concentration of less than about 100 µM, 50 µM, 10 µM, 1 µM, 0.1 µM, 0.05 µM, 0.01 µM, 0.005 µM, 0.001 µM, or less.

The disclosed therapeutic agents may be formulated as therapeutics for treating diabetes mellitus and/or non-alcoholic fatty liver disease. In some embodiments, the disclosed therapeutic agents are small molecule compounds. As such, compounds are disclosed herein for use in the disclosed methods and compositions. The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The therapeutic agents utilized in the methods disclosed herein may be formulated as pharmaceutical compositions that include: (a) a therapeutically effective amount of one or more therapeutic agents as disclosed herein; and (b) one or more pharmaceutically acceptable carriers, excipients, or diluents. The pharmaceutical composition may include the therapeutic agents in a range of about 0.1 to 2000 mg (preferably about 0.5 to 500 mg, and more preferably about 1 to 100 mg). The pharmaceutical composition may be administered to provide the therapeutic agent at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the therapeutic agent at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

In some embodiments of the disclosed treatment methods, the subject may be administered a dose of a therapeutic agent as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a therapeutic agent as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the therapeutic agent may include doses falling within dose ranges having as end-points any of these disclosed doses (e.g., 2.5 mg-200 mg).

In some embodiments, a minimal dose level of a therapeutic agent for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a therapeutic agent for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the therapeutic agent for achieving therapy in the disclosed methods of treatment may include dose levels falling within ranges having as end-points any of these disclosed dose levels (e.g., 500-2000 ng/kg body weight of the subject).

The therapeutic agent utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The disclosed therapeutic agent or pharmaceutical compositions comprising the disclosed therapeutic agent may be administered in methods of treatment. For example, the disclosed therapeutic agent or pharmaceutical compositions comprising the disclosed therapeutic agent may be administered in methods of treating and/or preventing diabetes mellitus and/or non-alcoholic fatty liver disease.

Optionally, the disclosed therapeutic agent that inhibit the biological activity of BCL6 or pharmaceutical compositions comprising the disclosed therapeutic agent that inhibits the biological activity of BCL6 may be administered with additional therapeutic agents, optionally in combination, in order to treat and/or prevent diabetes mellitus and/or non-alcoholic fatty liver disease. In some embodiments of the disclosed methods, one or more additional therapeutic agents are administered with the disclosed therapeutic agent that inhibits the biological activity of BCL6 or with pharmaceutical compositions comprising the disclosed therapeutic agent that inhibits the biological activity of BCL6, where the additional therapeutic agent is administered prior to, concurrently with, or after administering the disclosed therapeutic agent that inhibits the biological activity of BCL6 or the pharmaceutical compositions comprising the disclosed compounds. In some embodiments, the disclosed pharmaceutical composition are formulated to comprise the disclosed that therapeutic agent inhibits the biological activity of BCL6 and further to comprise one or more additional therapeutic agents, for example, one or more additional therapeutic agents for treating diabetes mellitus and/or non-alcoholic fatty liver disease.

B Cell Lymphoma Protein 6 (BCL6) as a Target for Treating Diabetes Mellitus and Non-alcoholic Fatty Liver Disease Disclosed are methods and compositions such as pharmaceutical compositions for treating and/or preventing diabetes mellitus (e.g., diabetes mellitus type 2). Also disclosed are methods and composition for treating and/or preventing non-alcoholic fatty liver disease. The disclosed methods utilize and the disclosed compositions utilize a therapeutic agent that inhibits the biological activity of B cell lymphoma protein 6 (BCL6). As such, the disclosed methods typically include administering to a subject in need thereof a therapeutic agent that inhibits the biological activity of B cell lymphoma protein 6 (BCL6).

The therapeutic agent may be administered by any suitable route of delivery. In some embodiments, the therapeutic agent is administered orally and/or the therapeutic agent has been modified or formulated to enhance oral bioavailability.

The therapeutic agent that is utilized in the disclosed methods typically inhibits the biological activity of BCL6. In some embodiments of the disclosed methods and compositions, the therapeutic agent induces degradation of BCL6. Compounds that induce the degradation of BCL6 are known in the art and include the compound referred to as BI-1136, which is an orally available compound that induces degradation of BCL6 and is available from Boehringer Ingelheim (See opnme.com/molecules/oral-bcl6-degrader; the content of which is incorporated herein by reference in its entirety). Boehringer Ingelheim has indicated that it will share BI-1136, which is a potent and selective orally bioavailable BCL6 degrader for collaborative research on novel disease indications. (See id.). BI-1136 potently inhibits the interaction of the BTB/POZ domain of BCL6 with several co-repressors in vitro ($IC_{50} \leq 50$ nM). (See id.). In a cellular context, the BCL6 degrader inhibits the BCL6:Co-repressor complex formation with an ICso of 210 nM. (See id.). Moreover, BI-1136 was found to be a potent and efficacious degrader of the BCL6 protein in mouse and human DLBCL cell lines ($DC_{50}$=63 nM in SU-DHL-4 cells) as well as in other BCL6 expressing cells tested (macrophages, NSCLC, Burkitt and breast cancer cell lines). (See id.). BI-1136 shows pharmacokinetic (PK) properties that are suitable for in vivo testing in several animal species and is well tolerated. (See also, Kerres et al., 2017, Cell Reports 20, 2860-2875; the content of which is incorporated herein by reference in its entirety.

In some embodiments, the therapeutic agent comprises a compound having a formula:

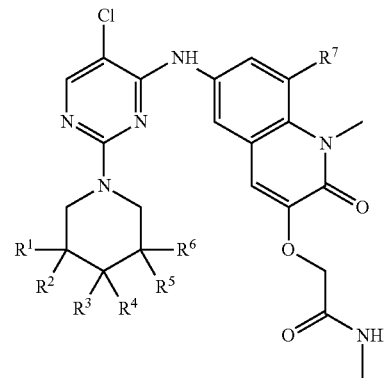

where:
$R^1$, $R^2$, $R^3$, $R^4$, $R^5$, and $R^6$ are the same or different and are selected from hydrogen, alkyl (e.g., methyl), halo (e.g., fluoro, chloro, bromo, or iodo), carboxyl (e.g., —C(O)OH), alkyl-morpholino (e.g., methyl-N-morpholino), carboxamido (e.g., —C(O)—N(CH$_3$)$_2$); and
$R^7$ is hydrogen, alkyl, alkoxy, or hydroxy.

In some embodiments of the disclosed methods and compositions, the therapeutic agent comprises a compound selected from the following compounds:

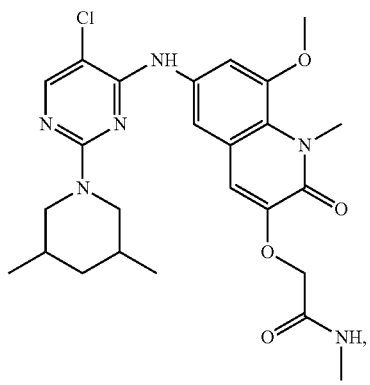

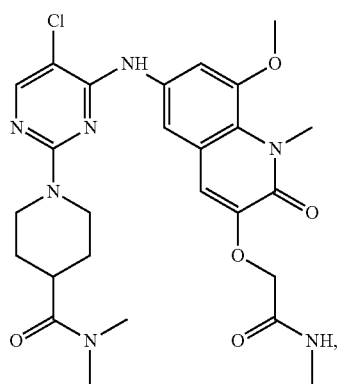
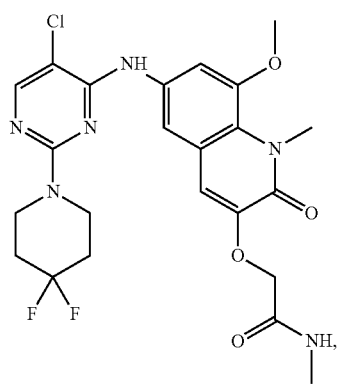
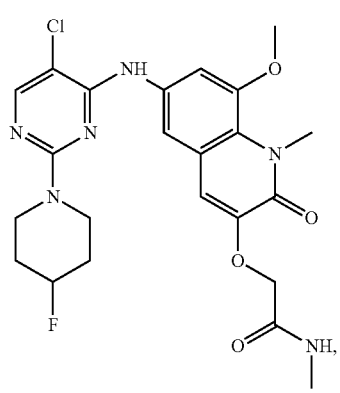
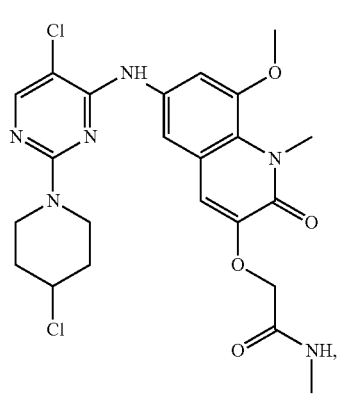
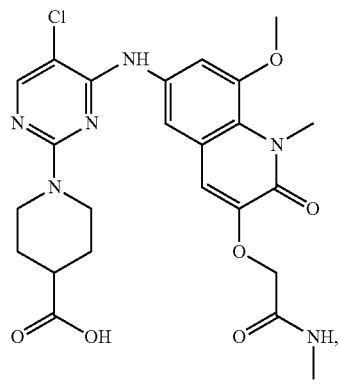
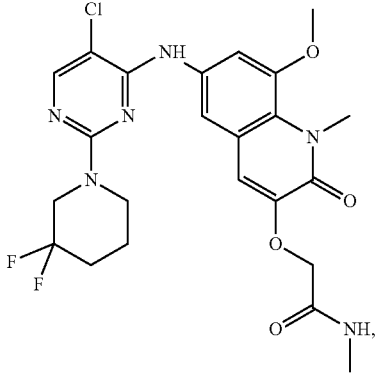
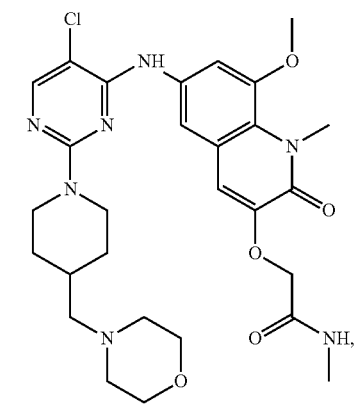
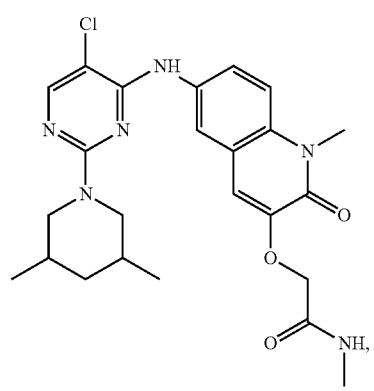

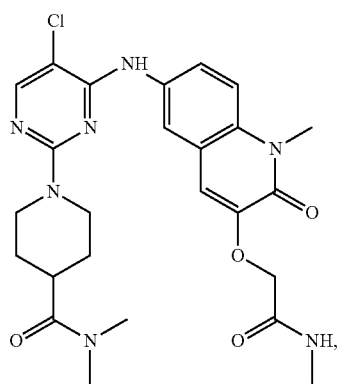
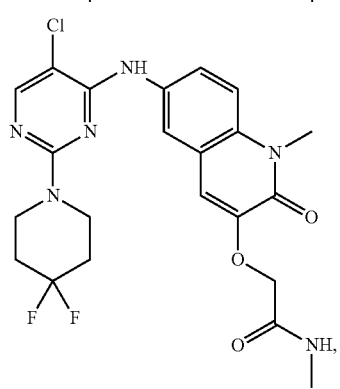
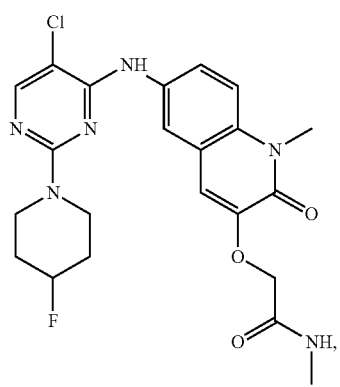
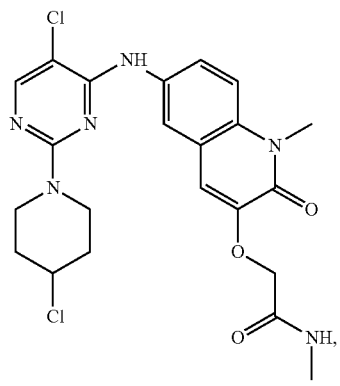
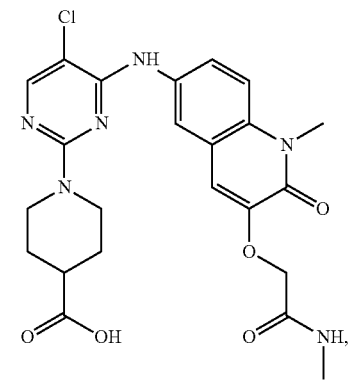
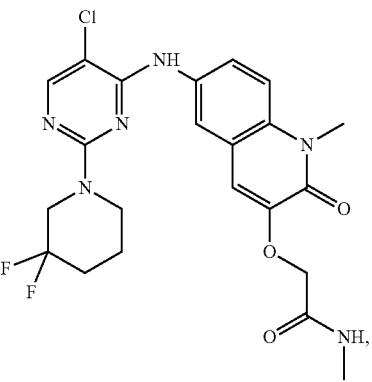
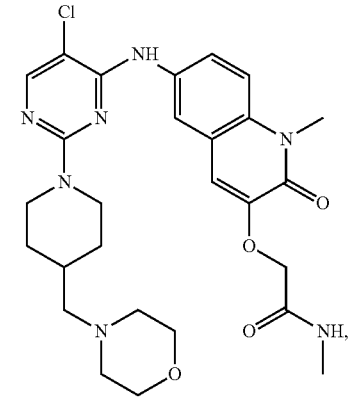
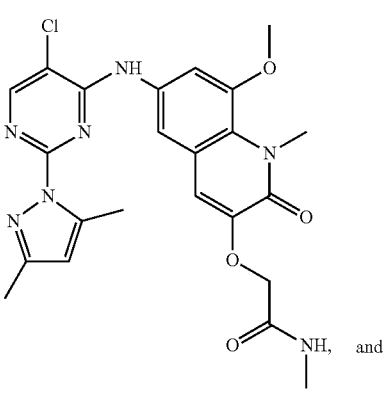
and -continued

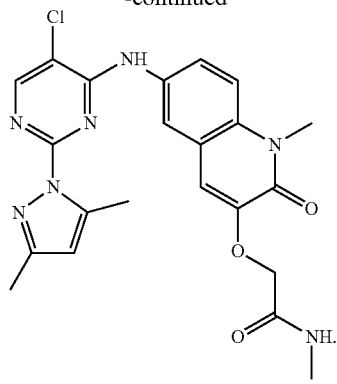

In some embodiments of the disclosed methods and compositions, the therapeutic agent of the disclosed methods and pharmaceutical compositions may disrupt formation of a BCL6 repression complex. The therapeutic agent may bind to BCL6, optionally at its corepressor binding groove of its BTB domain. Compounds that bind to BCL6 and inhibit and/or disrupt formation of a BCL6 repression complex are known in the art. (See Cardenas et al., "Rationally designed BCL6 inhibitors target activated B cell diffuse large B cell lymphoma," J. Clin. Invest. 2016; 126(9): 3351-3362; and Cerchietti et al., "A small molecule inhibitor of BCL6 kills DLBCL cells in vitro and in vivo," Cancer Cell. 2010 Apr. 13; 17(4):400-411; the contents of which are incorporated herein by reference in their entireties.)

In some embodiments, the therapeutic agents comprises a compound having a formula:

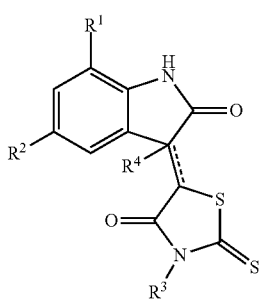

wherein:
$R^1$ and $R^2$ are the same or different and are selected from is selected from hydrogen, alkyl (e.g., methyl), alkoxy (e.g., methoxy), and nitro;
$R^3$ is hydrogen, carboxyalkyl or dicarboxyalkyl (e.g., dicarboxyethyl or CH(C(O)OH)—CH$_2$—C(O)OH, carboxymethyl or —CH$_2$—C(O)OH, or carboxyethyl or —CH$_2$—CH$_2$—C(O)OH), or —CH$_2$—CH$_2$—C(O)—N—CH$_2$—C(O)O—CH$_2$—CH$_3$.
$R^4$ is absent or present and when present $R^4$ is hydroxyl.

In some embodiments of the disclosed methods and compositions, the therapeutic agent comprises a compound selected from the following compounds:

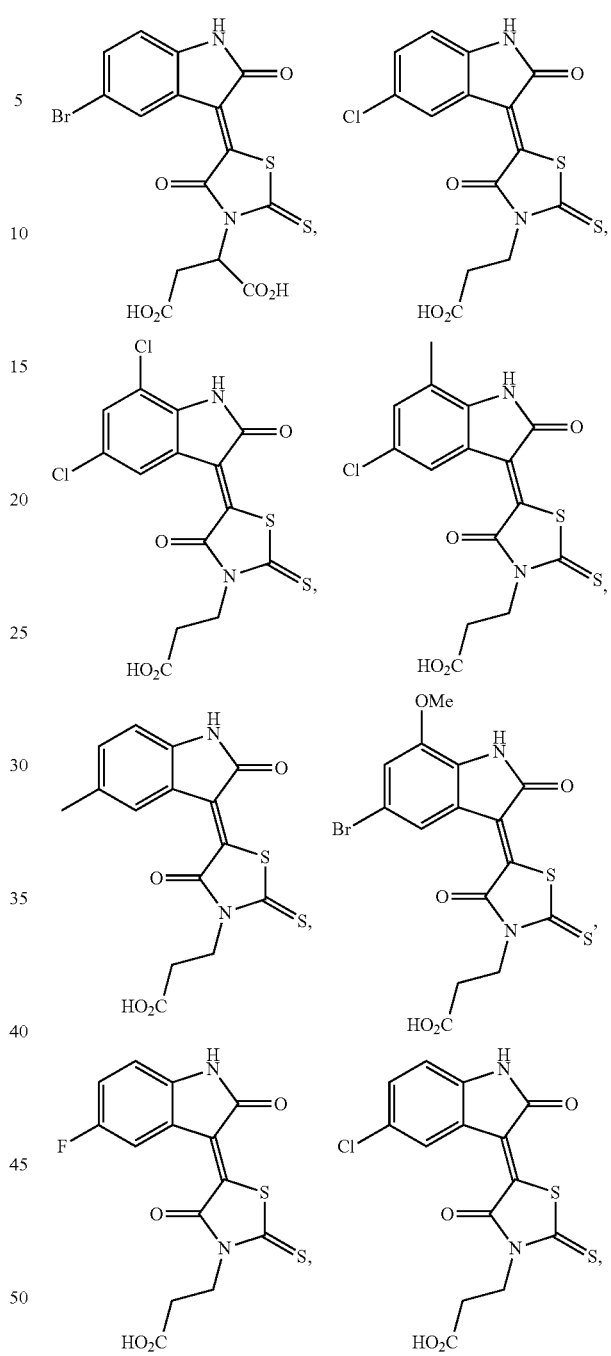

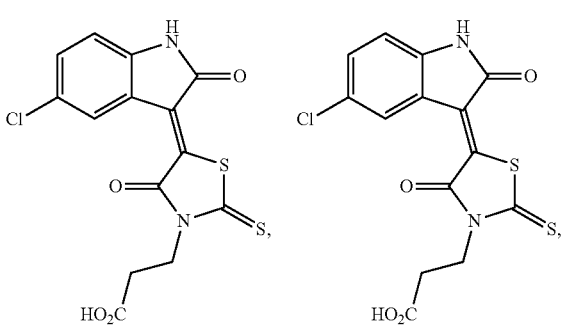

-continued

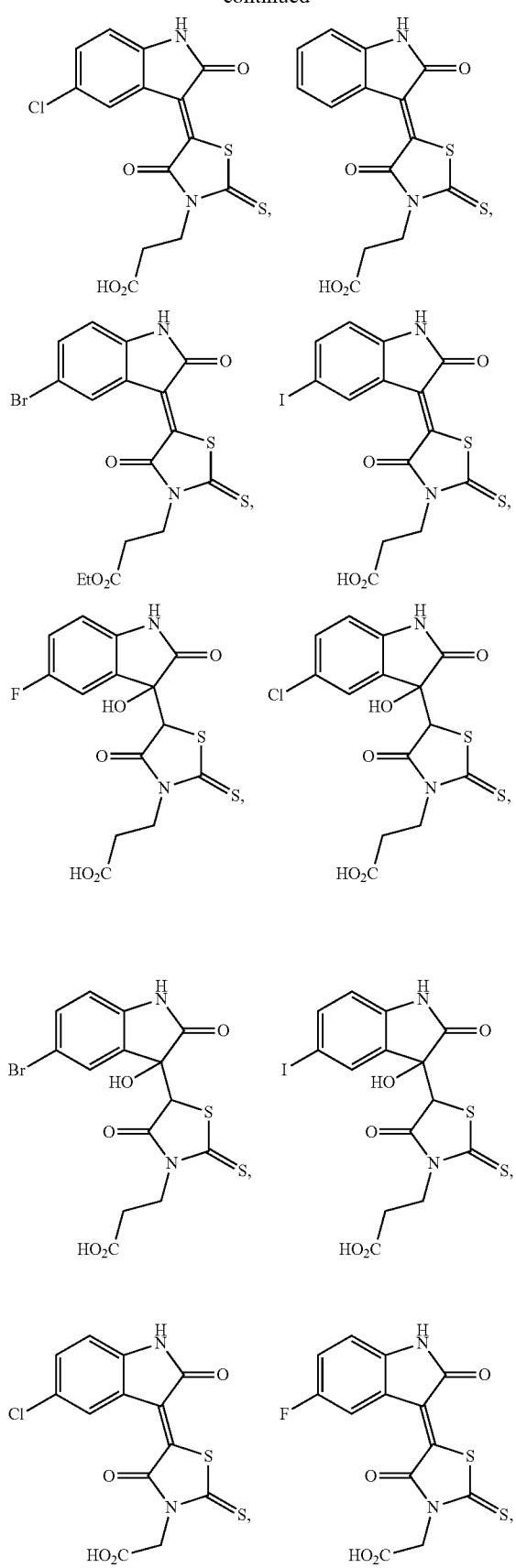
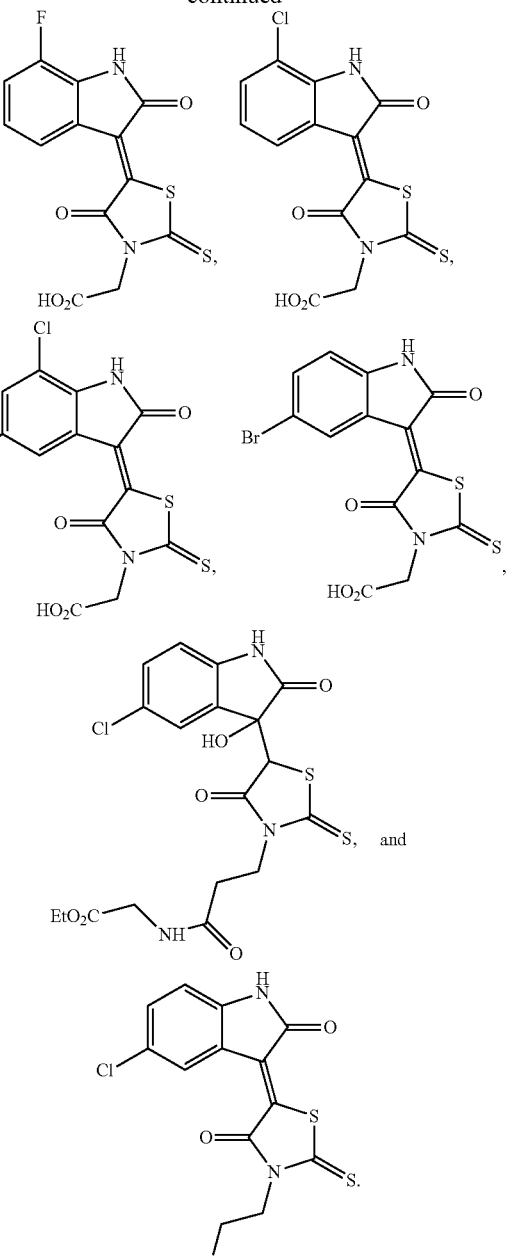

In other embodiments, the therapeutic agent is a compound selected from CID5723273, CID4298309, CID1150857, CID2187422, CID2162574, CID1087015, CID6841841, CID2006902, and CID5513673.

In some embodiments of the disclosed methods and compositions, the therapeutic agent inhibits methylation of BCL6. Compounds that inhibit methylation of BCL6 are known in the art. (See Lu et al., "PRMT5 interacts with the BCL6 oncoprotein and is required for germinal center formation and lymphoma cell survival," Blood, 2018; 132 (19):2026-2039; the content of which is incorporated herein by referenced in its entirety). Optionally, the therapeutic agent may inhibit methylation of BCL6 by protein arginine methyltransferase 5 (PRMT5) at arginine 305.

In some embodiments, the therapeutic agent is a compound having a formula:

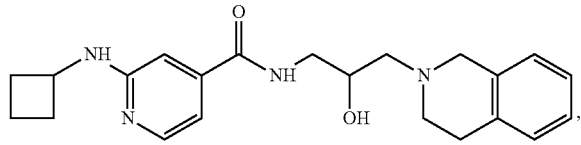 [SMILES: O=C(NCC(O)CN1CCc2ccccc2C1)c1ccnc(NC2CCC2)c1]

which otherwise may be referred to as GSK591 (APExBIO).

EXAMPLES

The following Example is illustrative and is not intended to limit the claimed subject matter.

Example 1

Title: BCL6 degradation for non-alcoholic fatty liver disease and diabetes mellitus Abstract Non-alcoholic fatty liver disease (NAFLD) is an increasingly prevalent disorder with no approved drug treatment. It occurs with a spectrum of pathological severity including fatty liver, steatohepatitis, and steatonecrosis, which can lead to cirrhosis and hepatocellular carcinoma [1-3]. It is currently estimated that over 64 million people in the United States have NAFLD, while in Germany, France, Italy, and the United Kingdom combined there are ~52 million with NAFLD [4]. The associated annual direct medical costs are $103 billion and €35 billion, respectively. NAFLD is also highly associated with obesity, cardiovascular disease, and diabetes mellitus, the latter of which afflicts up to ~10% of the U.S. and European populations and over 422 million people worldwide [5]. In the United States alone, the directly associated medical cost of diabetes mellitus is $237 billion per year [6].

We have made surprising discoveries regarding the role for BCL6 in metabolic control which have novel implications for NAFLD therapeutics via BCL6 reduction or inhibition [7, 8]. Genetic ablation of Bcl6 confers protection against insulin resistance and steatosis, raising the possibility that small molecules to degrade BCL6 could be therapeutic for obesity-related metabolic pathologies including type 2 diabetes mellitus and non-alcoholic fatty liver disease. We propose that reducing BCL6 levels will ameliorate obesity-related conditions including non-alcoholic fatty liver disease and type 2 diabetes mellitus.

Although best recognized for its critical roles in B cell development and lymphomagenesis, BCL6 is broadly expressed in non-immune tissues wherein its functions are poorly understood. To address this gap, my laboratory has developed many unique mouse tissue-specific models, including adipocyte-specific and hepatocyte-specific Bcl6 knockouts. We have also developed a Rosa26 knockin model containing a CMV promoter and a loxP-flanked stop cassette upstream of a V5 and polyhistidine-tagged Bcl6 transgene, allowing us to overexpress Bcl6 in a cell-type specific manner. Additionally, we have developed custom polyclonal antibodies to mouse BCL6, which we have used extensively for BCL6 ChIP-sequencing in various mouse tissues and cell types. In conjunction with my division's infrastructure for genomics and metabolic phenotyping, we have deployed these reagents to reveal new and powerful regulatory roles for BCL6 outside of the immune system. Boehringer Ingelheim's orally available small molecule compound BI-1136, used with our model systems and capabilities for metabolic testing, will allow us to further establish BI-1136's target specificity while determining whether BCL6 degradation could be therapeutic for metabolic disease.

Results

Selective developmental ablation of Bcl6 in adipocytes (Bcl6$^{AKO}$ mice) enhanced the expression of growth and lipid biosynthetic genes leading to subcutaneous adipose tissue expansion, yet it improved whole-body insulin sensitivity and reduced hepatic lipid content (FIG. 1)[7]. As illustrated in FIG. 1, mice with constitutive (in utero) deletion of Bcl6 in adipocytes are insulin sensitive and are protected from the development of steatosis (fatty liver) when subjected to high fat diet.

Figure 2:
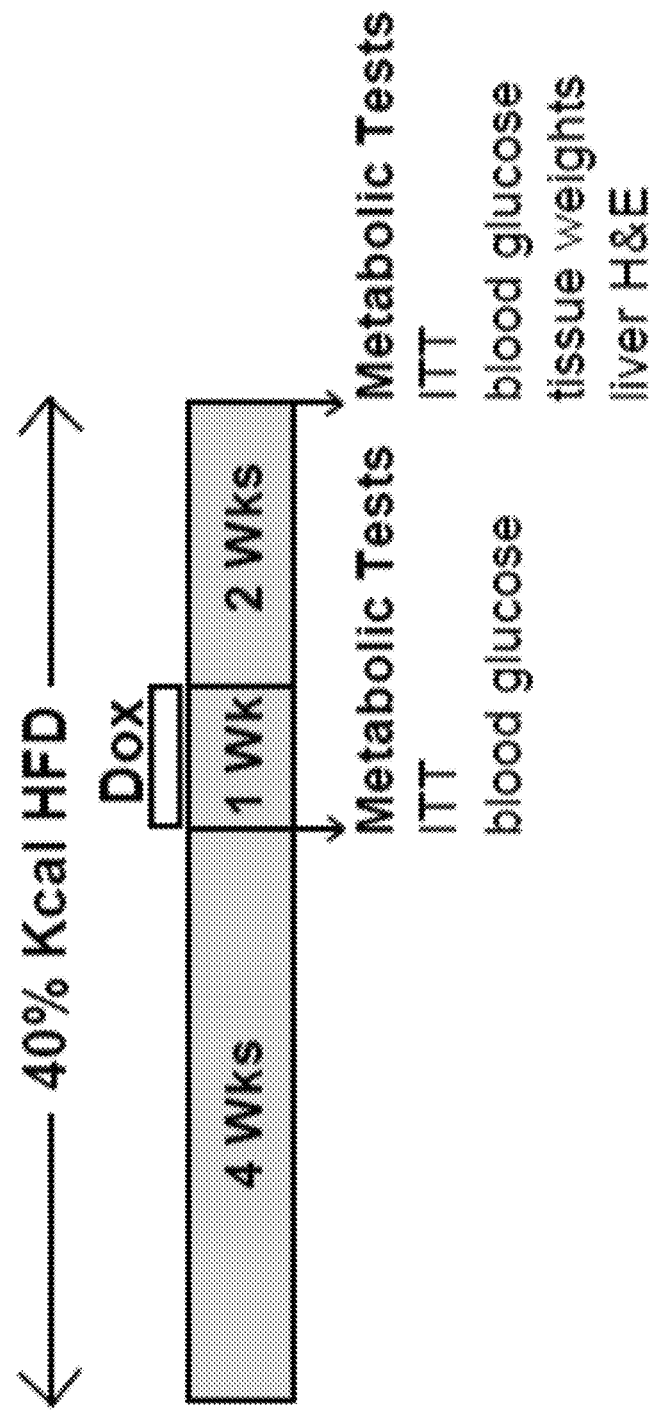
FIG. 2. Inducible deletion of adipocyte Bcl6 in adult mice leads to insulin sensitivity and protects from hepatic steatosis. (A) Adult control and Bcl6$^{fl/fl}$ mice with doxycycline-inducible Cre transgenes (Bcl6$^{iAKO}$) at 9-10 weeks of age were fed high fat diet for four weeks, treated with doxycycline (Dox), and subjected to metabolic testing over a seven week experimental period. (B) Pre-doxycyline treatment (left, after 4 weeks of high fat diet) and post-doxycycline treatment (right, after 7 weeks of high fat diet) fasting glucose levels. N=8 per group (C) Pre-doxycyline treatment insulin tolerance testing in control and Bcl6$^{iAKO}$ mice, performed after 4 weeks of high fat diet. N=8 per group (D) Post-doxycyline treatment insulin tolerance testing in control and Bcl6$^{iAKO}$ mice, performed after 7 weeks of high fat diet. N=8 per group (E) Body and tissue weights in control and Bcl6$^{iAKO}$ mice after 7 weeks of high fat diet. N=6-8 per group (F) Hematoxylin and eosin stained tissue sections of representative livers and inguinal subcutaneous adipose tissue depots from control and Bcl6$^{iAKO}$ mice after 7 weeks of high fat diet. Reduced hepatocyte steatosis and expanded adipocytes were observed in Bcl6$^{iAKO}$ mice. A two-tailed Student's t-test assuming equal variance was used to compare means between two groups. Data are represented as mean±SEM. *p<0.05, **p<0.01.
Figure 2:
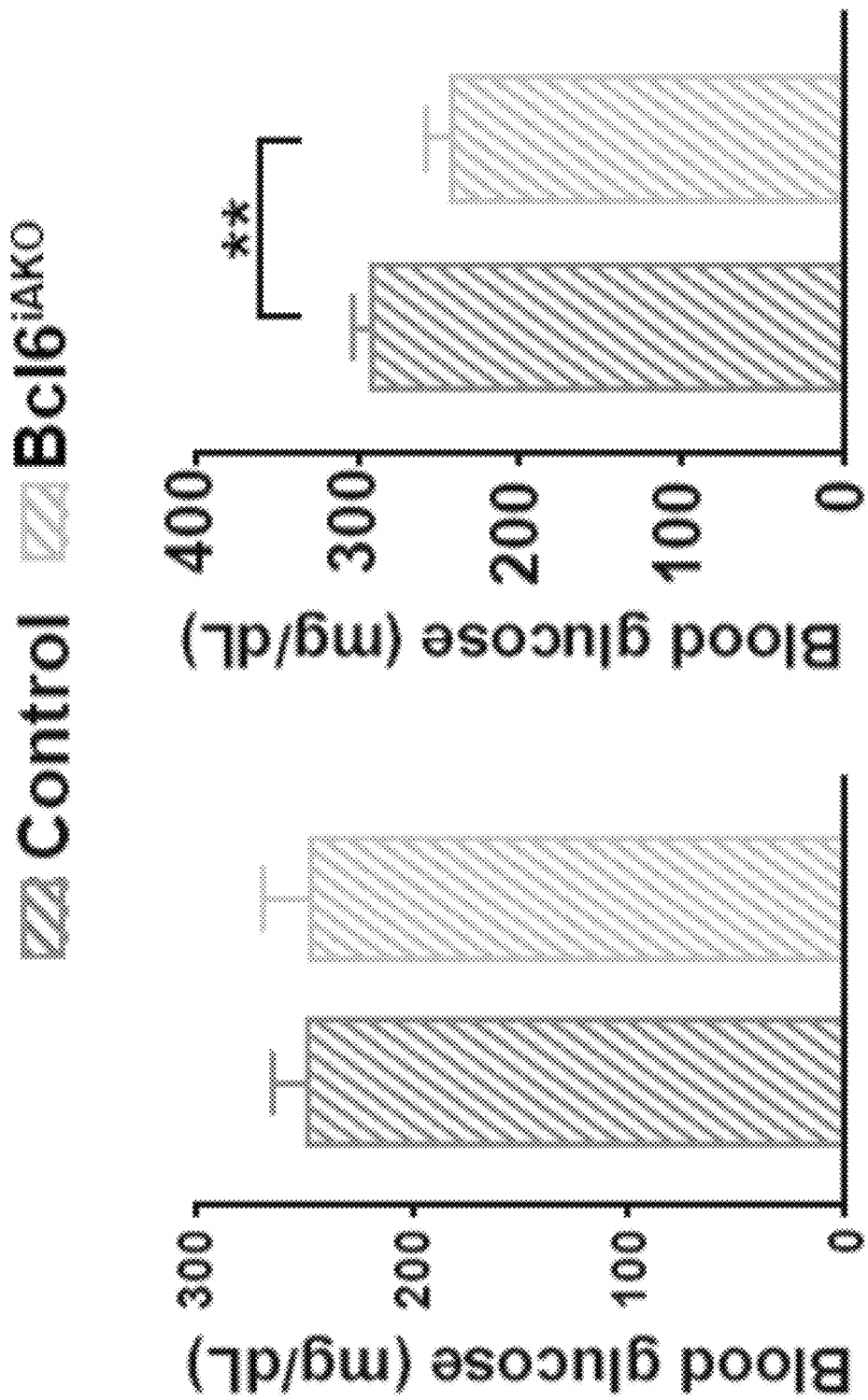
Figure 2:
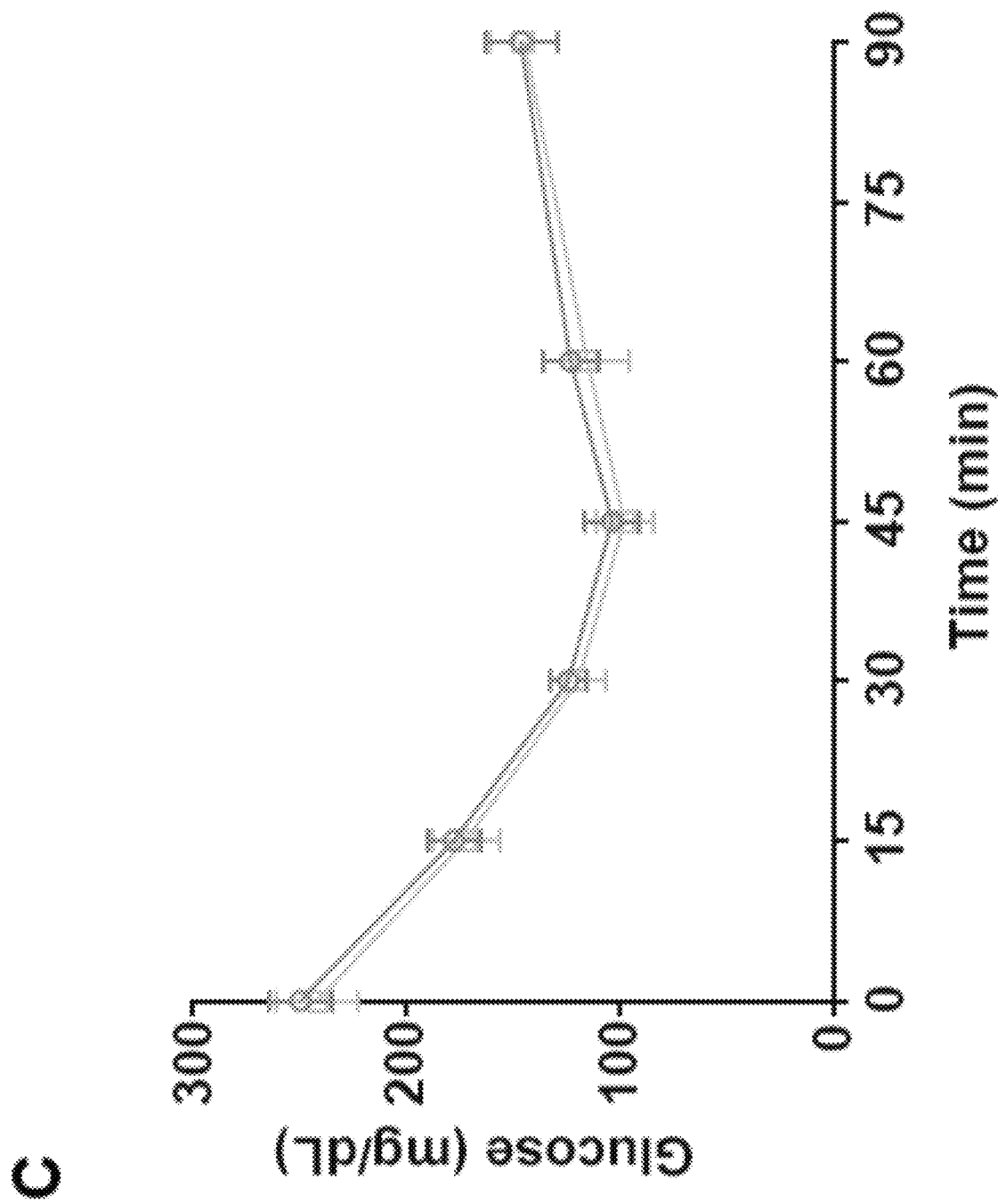
Figure 2:
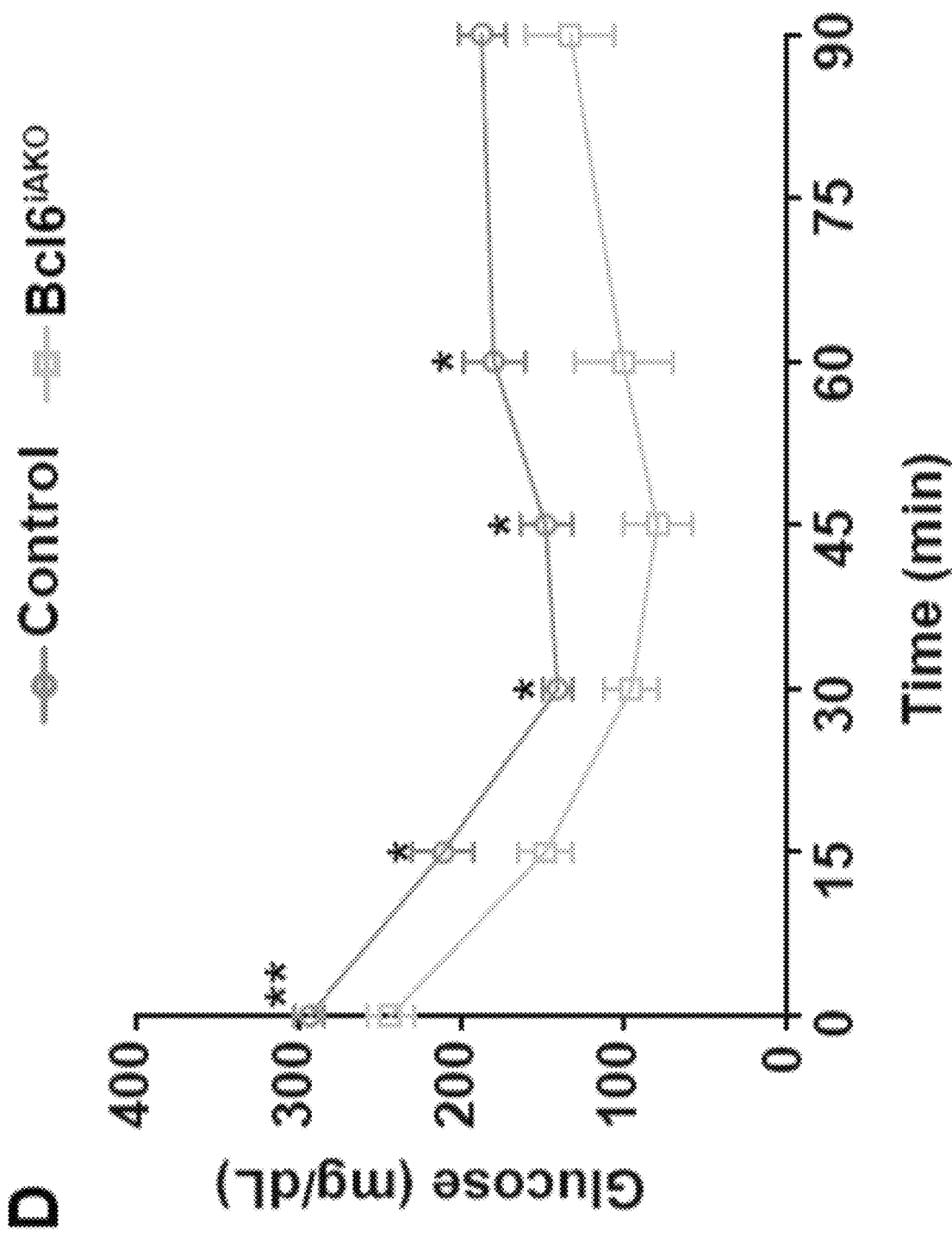
Figure 2:
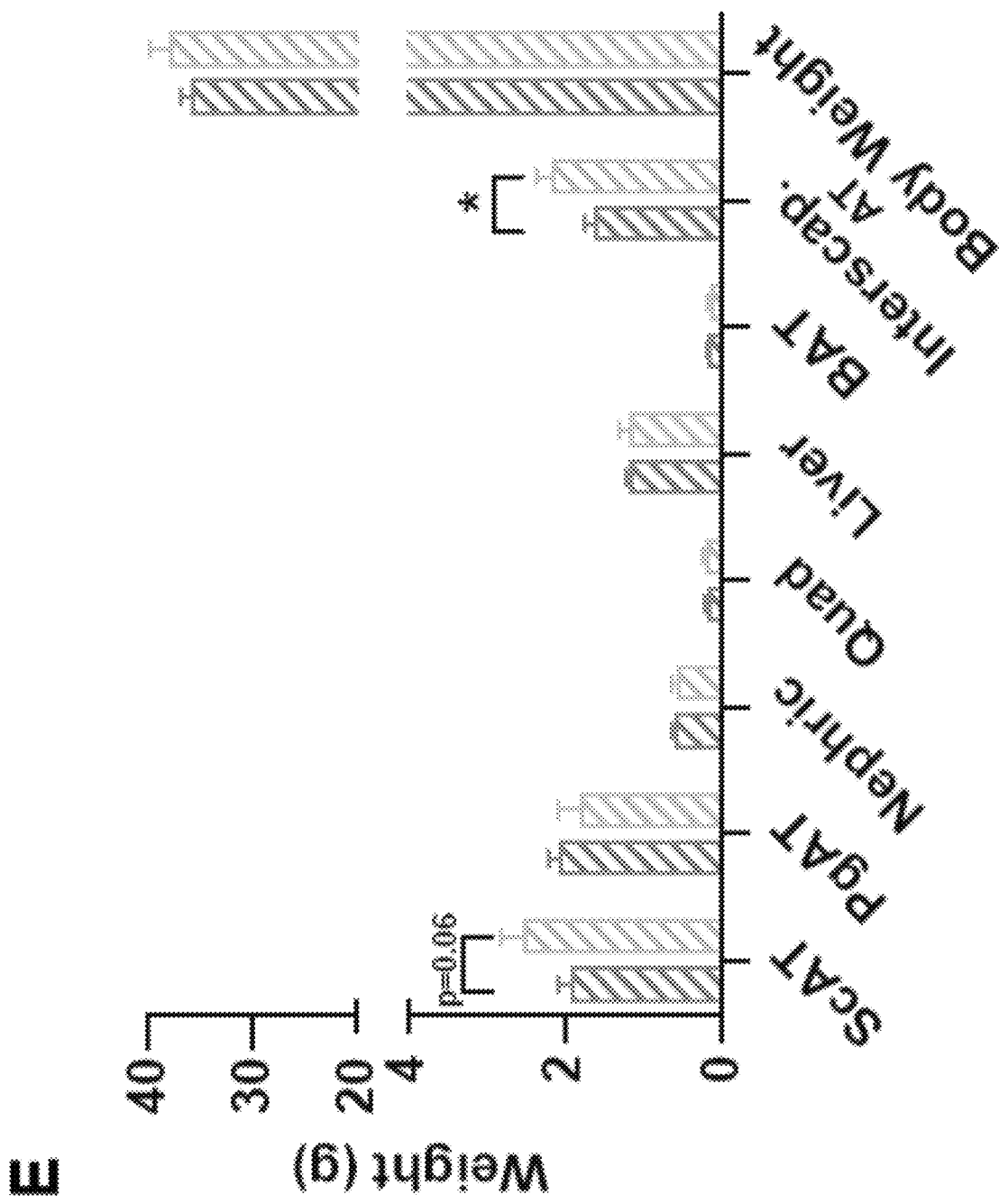
Figure 2:
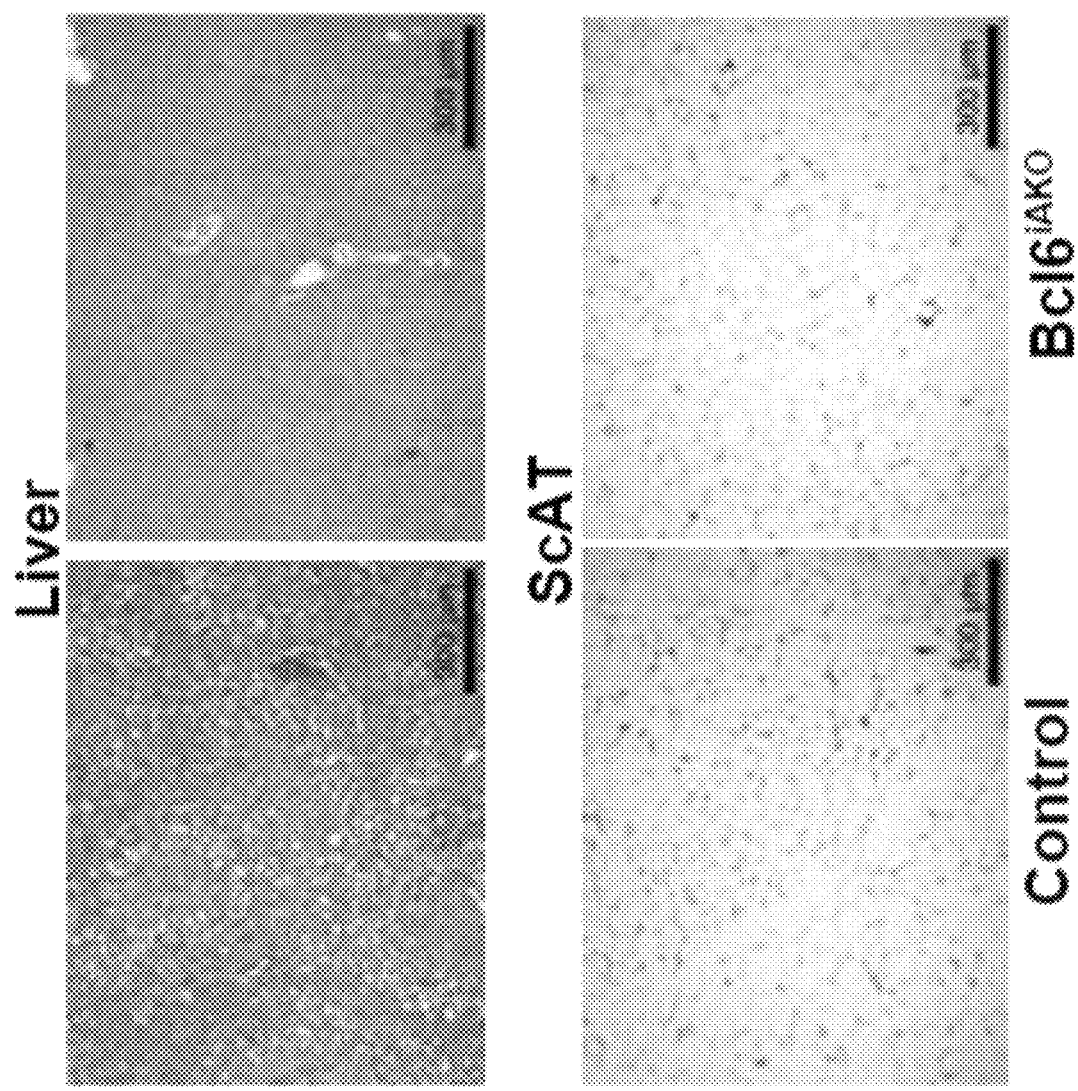

In liver, BCL6 converges genome-wide with peroxisome proliferator activated receptor alpha (PPARa), a master regulator of lipid catabolism (FIG. 2). Selective deletion of Bcl6 in hepatocytes (Bcl6$^{LKO}$ mice) promoted fatty acid oxidation and protected mice from developing steatosis and hepatic insulin resistance on a high-fat diet [8]. As illustrated in FIG. 2, obese adult mice that are treated with doxycycline to inducibly delete Bcl6 in adipocytes rapidly become insulin sensitive and have reduced fatty liver.

Figure 3:
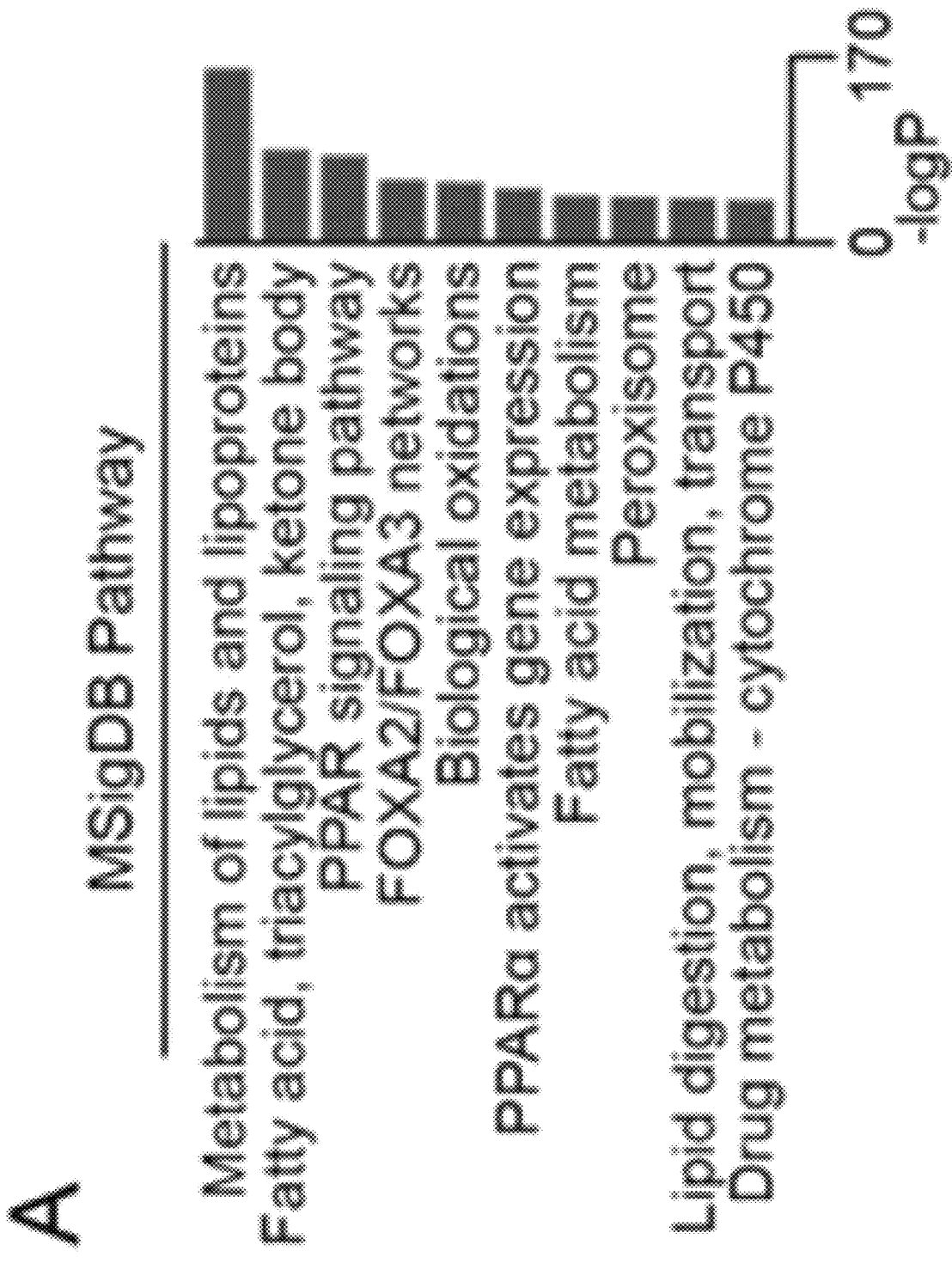
FIG. 3. BCL6 represses PPARα-controlled genes to suppress fatty acid oxidation and promote steatosis. (A) MSigDB Pathway of BCL6 ChIP-seq binding sites. (B) Motif enrichment analysis of BCL6 bound regions. (C) Venn diagrams comparing the overlap between liver ChIP-seq peaks for BCL6 and PPARα (based on a distance between peak centers of <200 bp). (D) Serum β-hydroxybutyrate levels measured in mice over the course of a 48-hour fast. N=8-12 per group. (E) Rates of $^{14}$C-palmitate oxidation in Bcl6$^{fl/fl}$ (control) and Bcl6$^{iAKO}$ (Bcl6 liver-specific knockout) liver homogenates measured in $CO_2$ and acid soluble fractions. N=3 per group. (F) Oil Red O staining in livers. (G) Biochemical quantification of liver triglycerides. (H-I) Overnight fasted serum (H) glucose and (I) insulin in Bcl6$^{fl/fl}$ and Bcl6$^{LKO}$ mice at 17 weeks on high fat diet. N=6-9 per group. (J) Western blots showing phosphorylated AKT (pAKT) and total AKT (panAKT) protein levels following injection of insulin in Bcl6$^{fl/fl}$ and Bcl6$^{LKO}$ livers after 5 weeks on HFD. MemCode™ membrane staining is used as the loading control. Data are represented as mean±SEM. *p<0.05, p<0.01, *p<0.001
Figure 3:
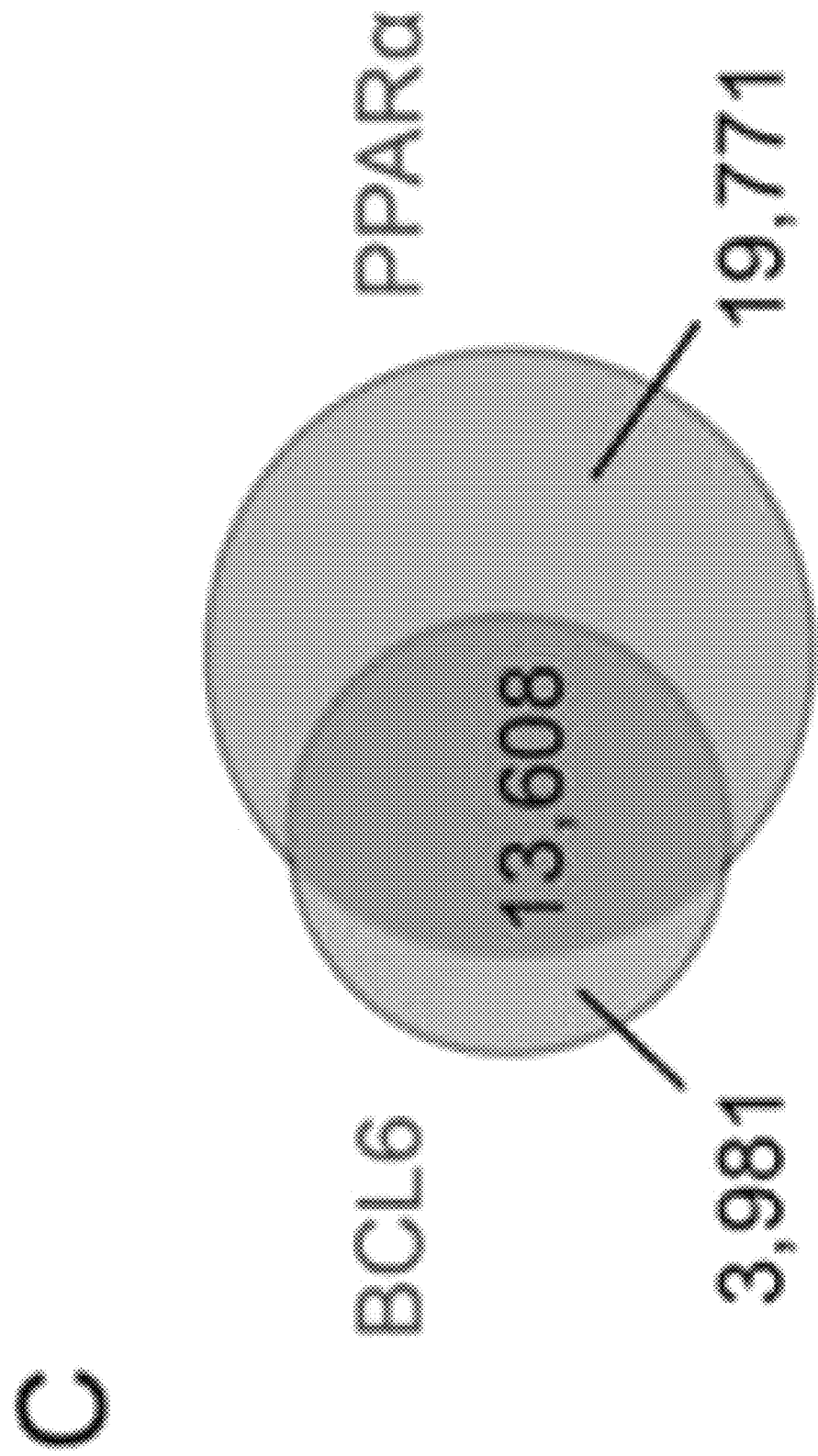
Figure 3:
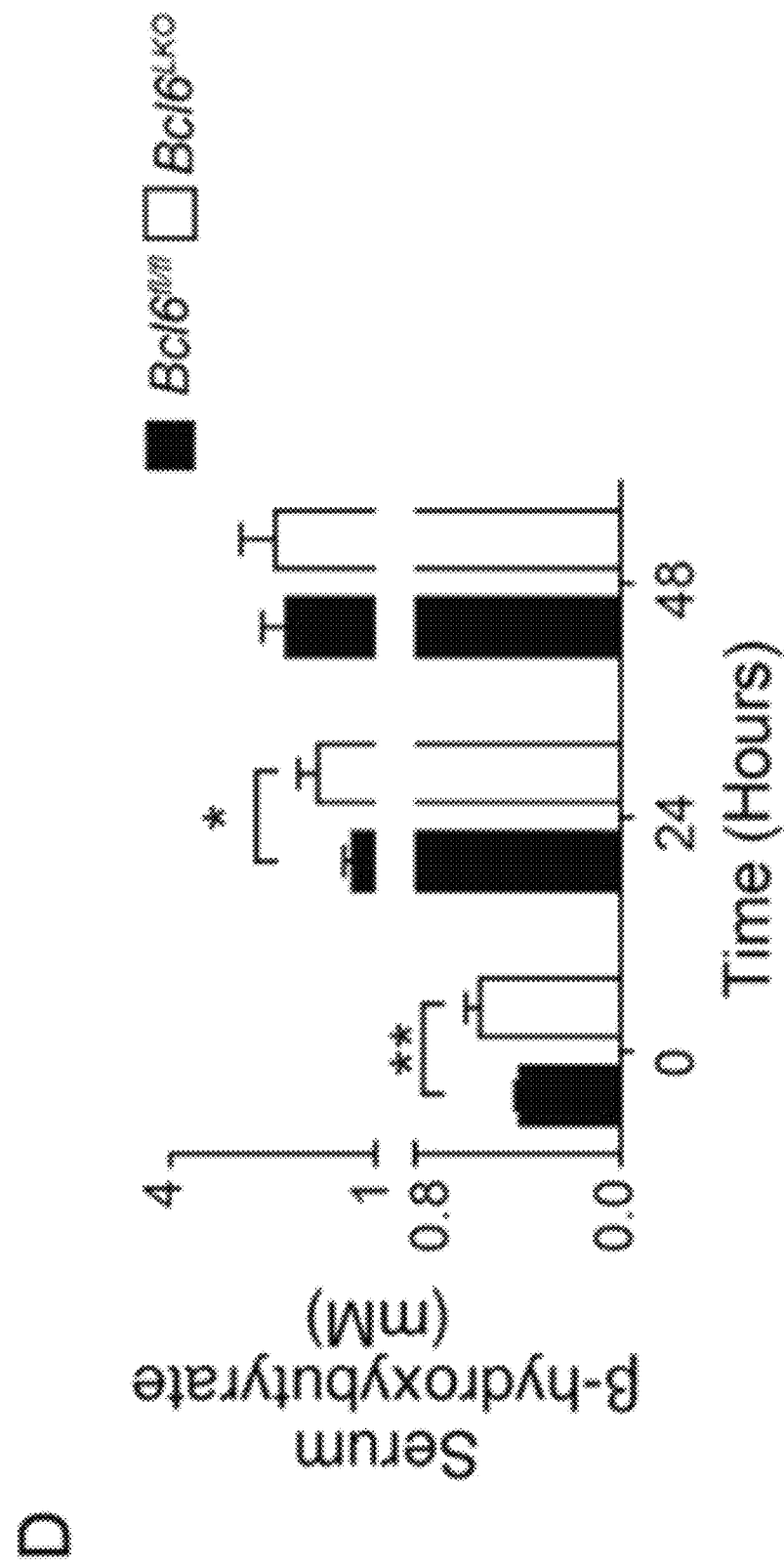
Figure 3:
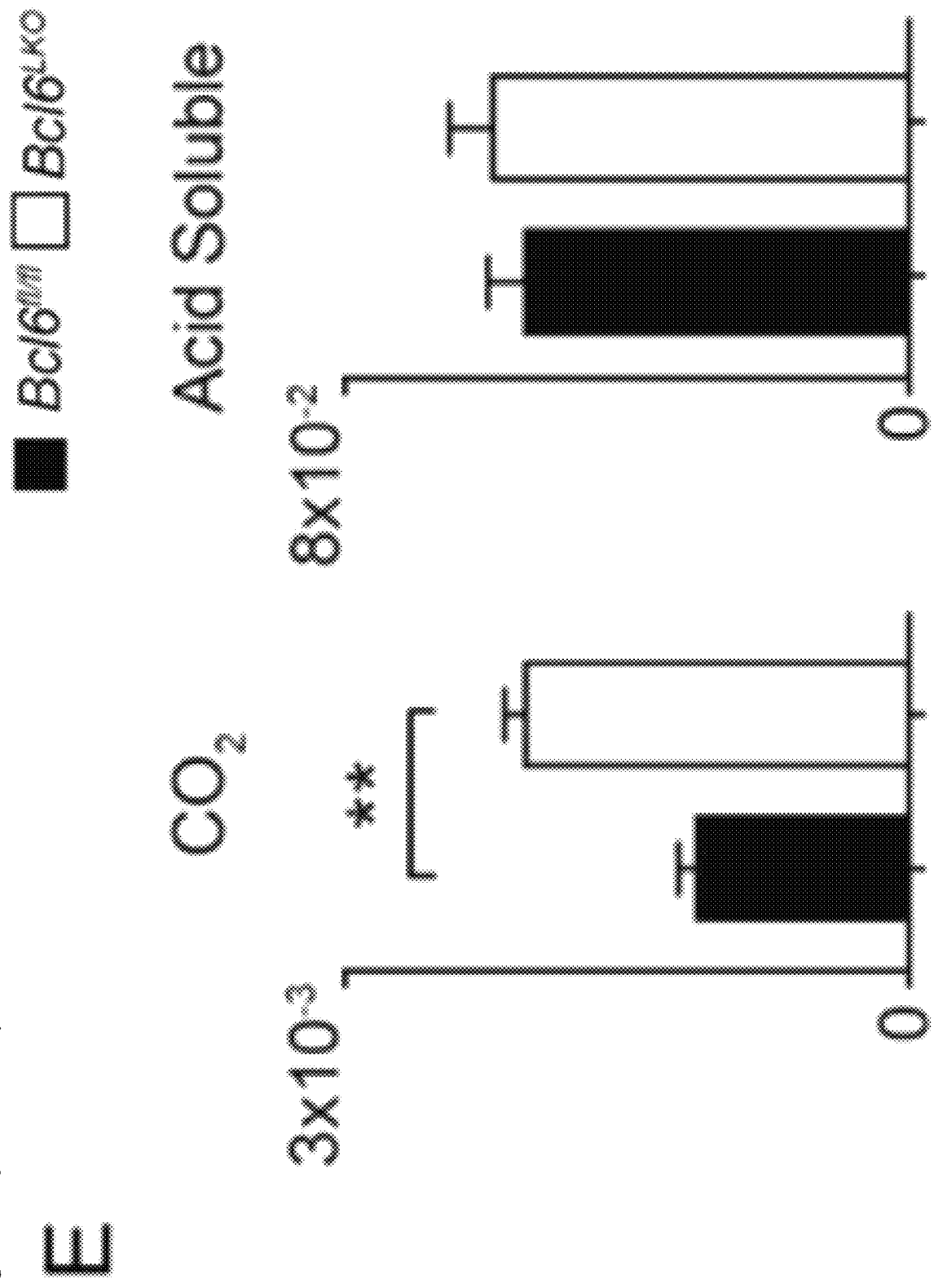
Figure 3:
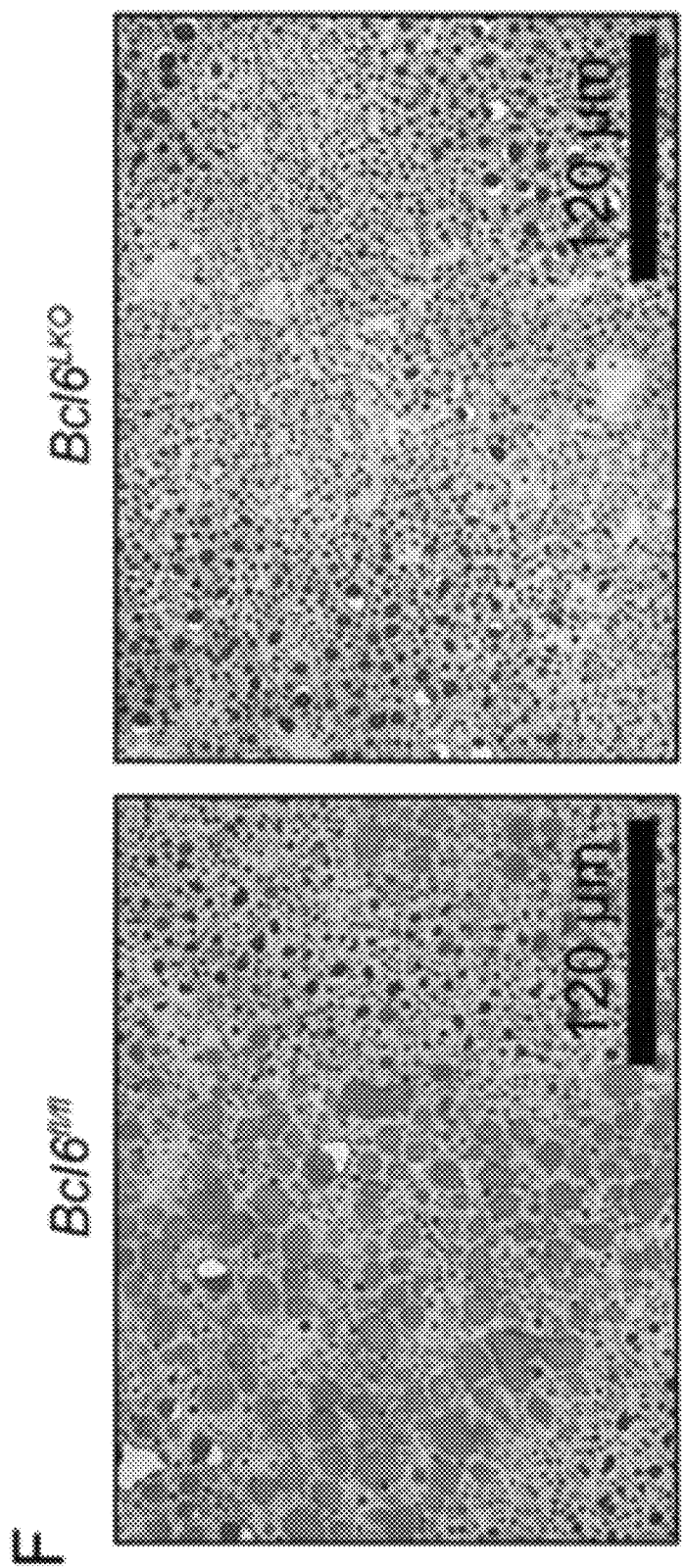
Figure 3:
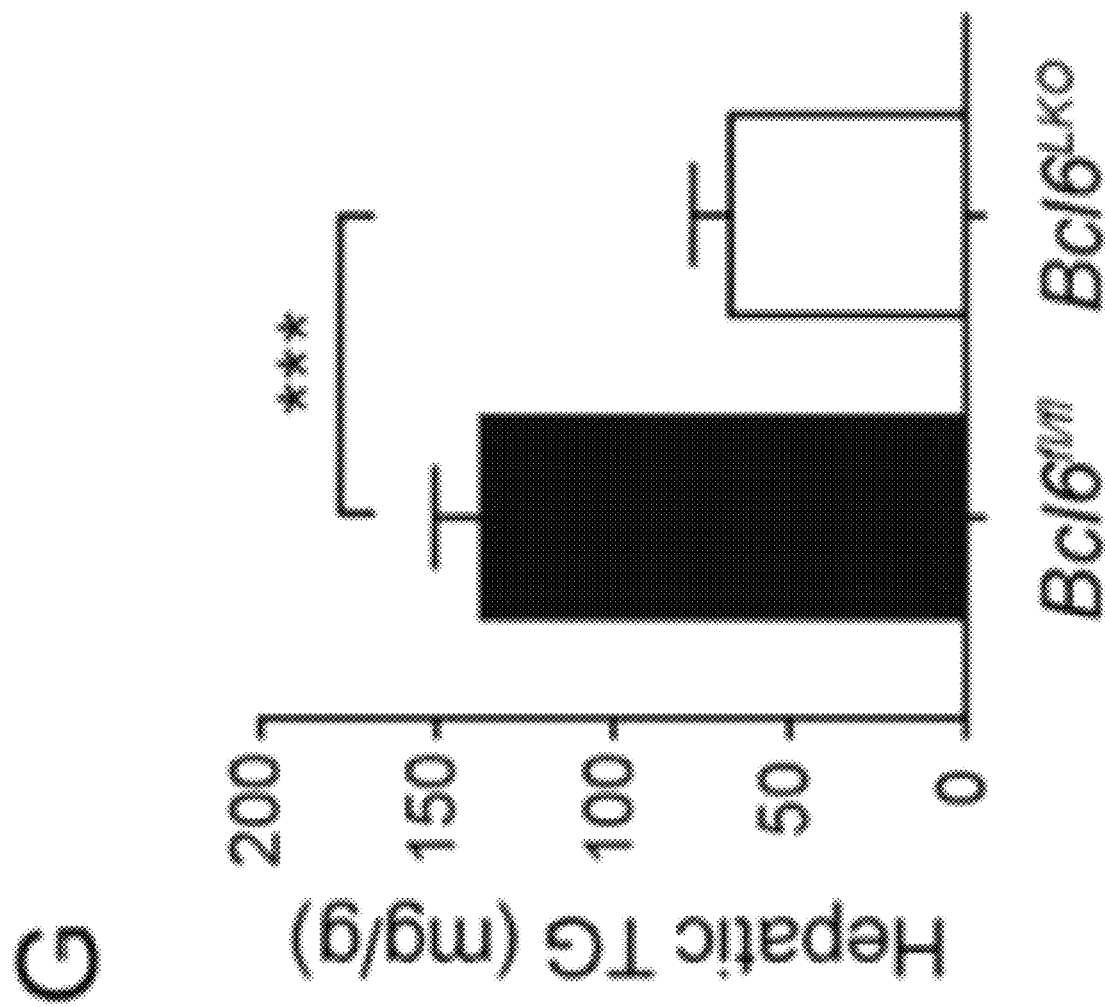
Figure 3:
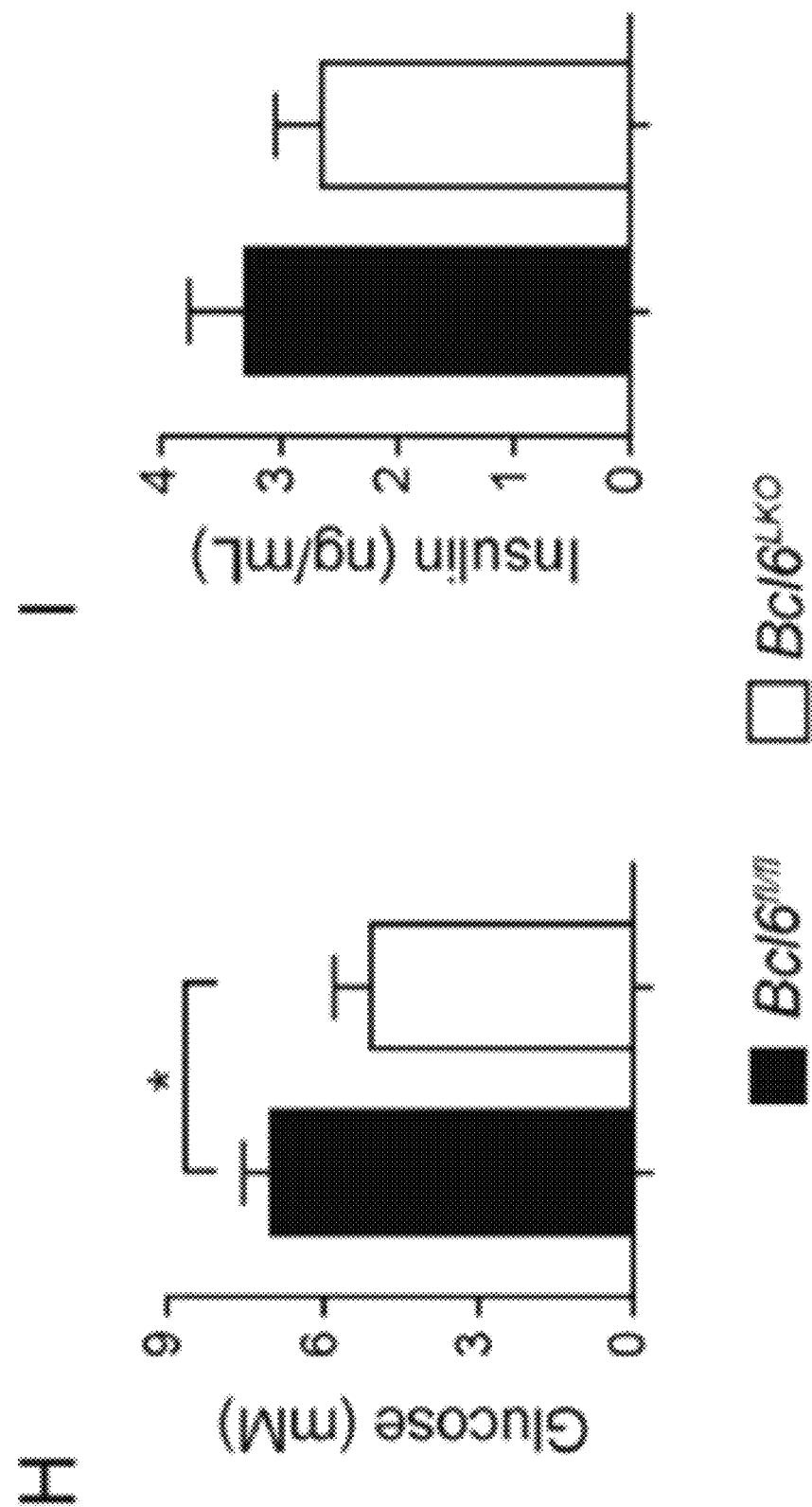
Figure 3:
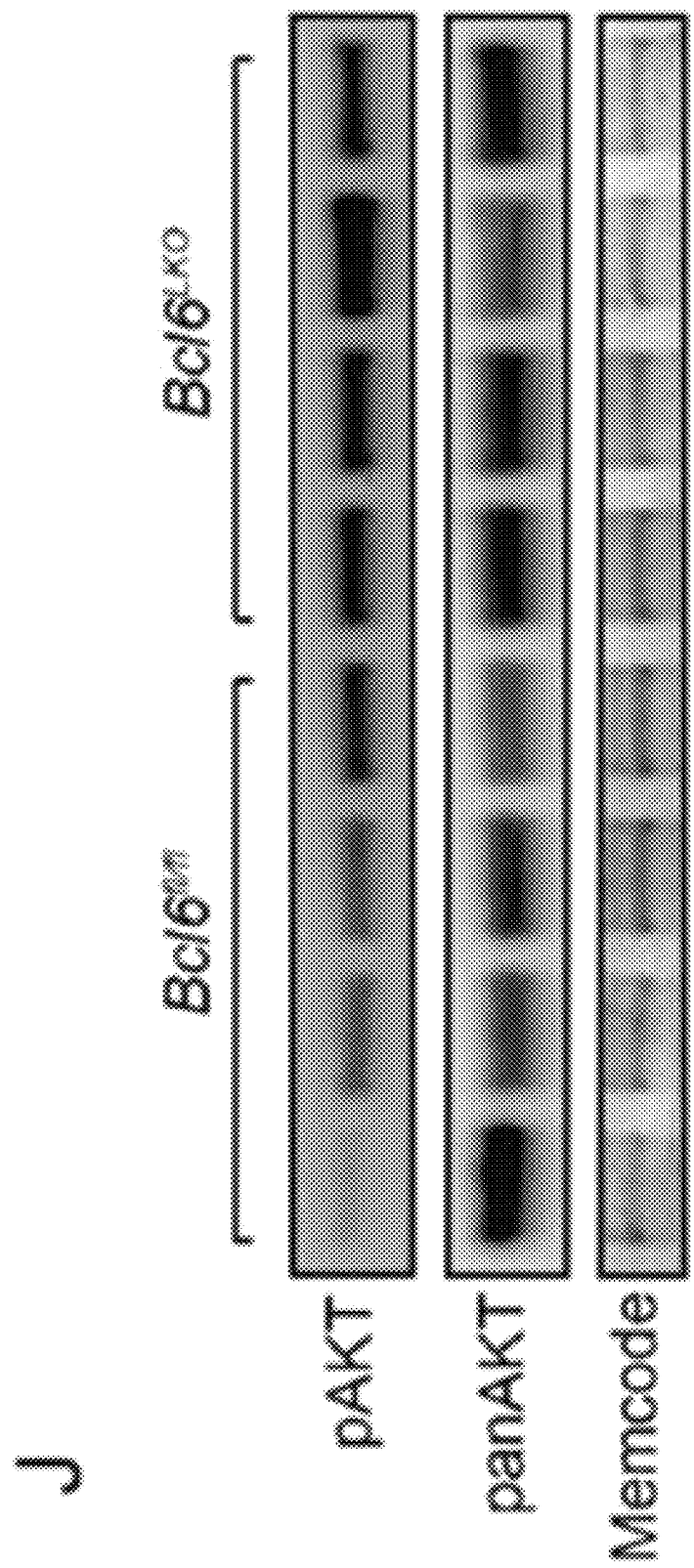

As illustrated in FIG. 3, mice with constitutive (in utero) deletion of Bcl6 in hepatocytes have enhanced capacity to burn fatty acids and are protected from developing fatty liver when subjected to high fat diet. They also demonstrate reduced fasting blood glucose and insulin level and a trend toward increased insulin sensitivity based upon insulin signaling assays examining inducible phosphorylation of AKT.

Figure 4:
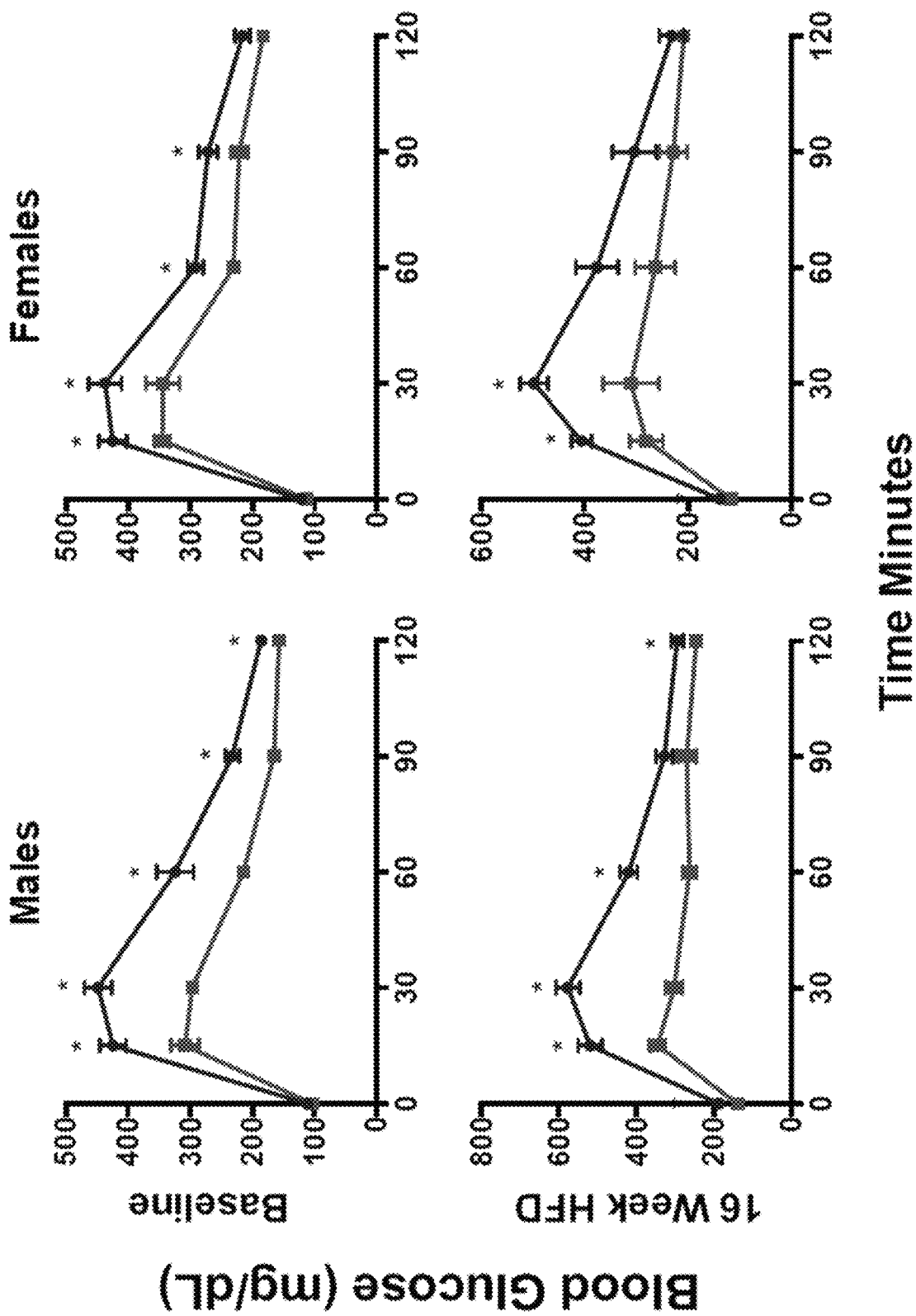
FIG. 4. Genetic deletion of hepatocyte Bcl6 markedly enhances glucose tolerance. Blood glucoses following intraperitoneal glucose (2 g/kg) in control (Bcl6$^{fl/fl}$) and hepatocyte-specific Bcl6 knockout (Bcl6$^{LKO}$) mice on regular chow diet (top) or after 15 weeks of 45% high fat diet (HFD, bottom) are shown in males (left) and females (right). N=7-9 per group. A two-tailed Student's t-test assuming equal variance was used to compare means between two groups. Data are represented as mean±SEM. *p<0.05, p<0.01, *p<0.001. Control mice and Bcl6$^{LKO}$ mice are indicated.

As illustrated in FIG. 4, male and female mice with constitutive deletion of Bcl6 in hepatocytes have markedly improved glucose tolerance, either when consuming standard chow or high fat diets.

Figure 5:
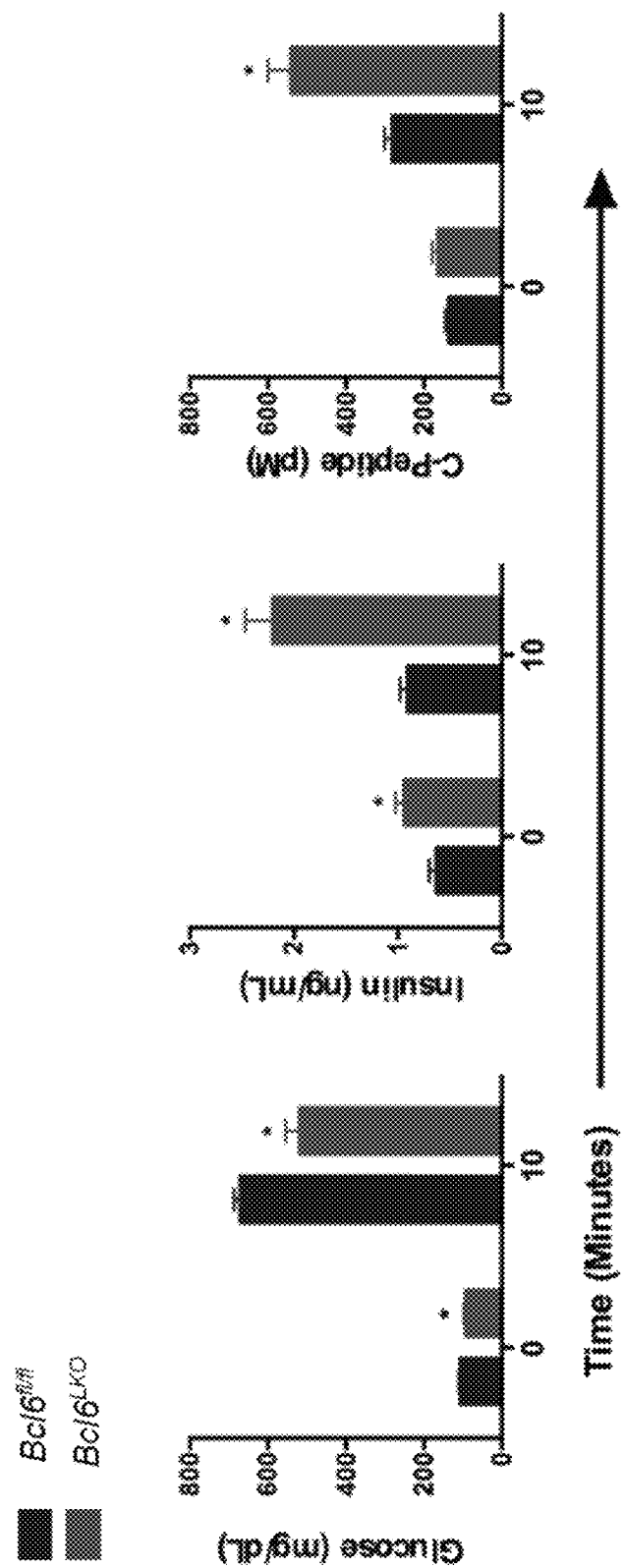
FIG. 5. Loss of Bcl6 in hepatocytes enhances glucose-stimulated insulin secretion. Acute insulin secretory responses were tested in wild type control mice (Bcl6$^{fl/fl}$) and Bcl6 hepatocyte-specific knockout mice (Bcl6$^{LKO}$) following intraperitoneal injection of glucose (3 g/kg). Ten minutes after glucose injection, insulin and C-peptide levels were significantly increased while glucose levels were significantly reduced in Bcl6$^{LKO}$ mice. *p<0.05.

As illustrated in FIG. 5, mice with constitutive deletion of Bcl6 in hepatocytes demonstrate increased glucose-stimulated insulin secretion.

Figure 6:
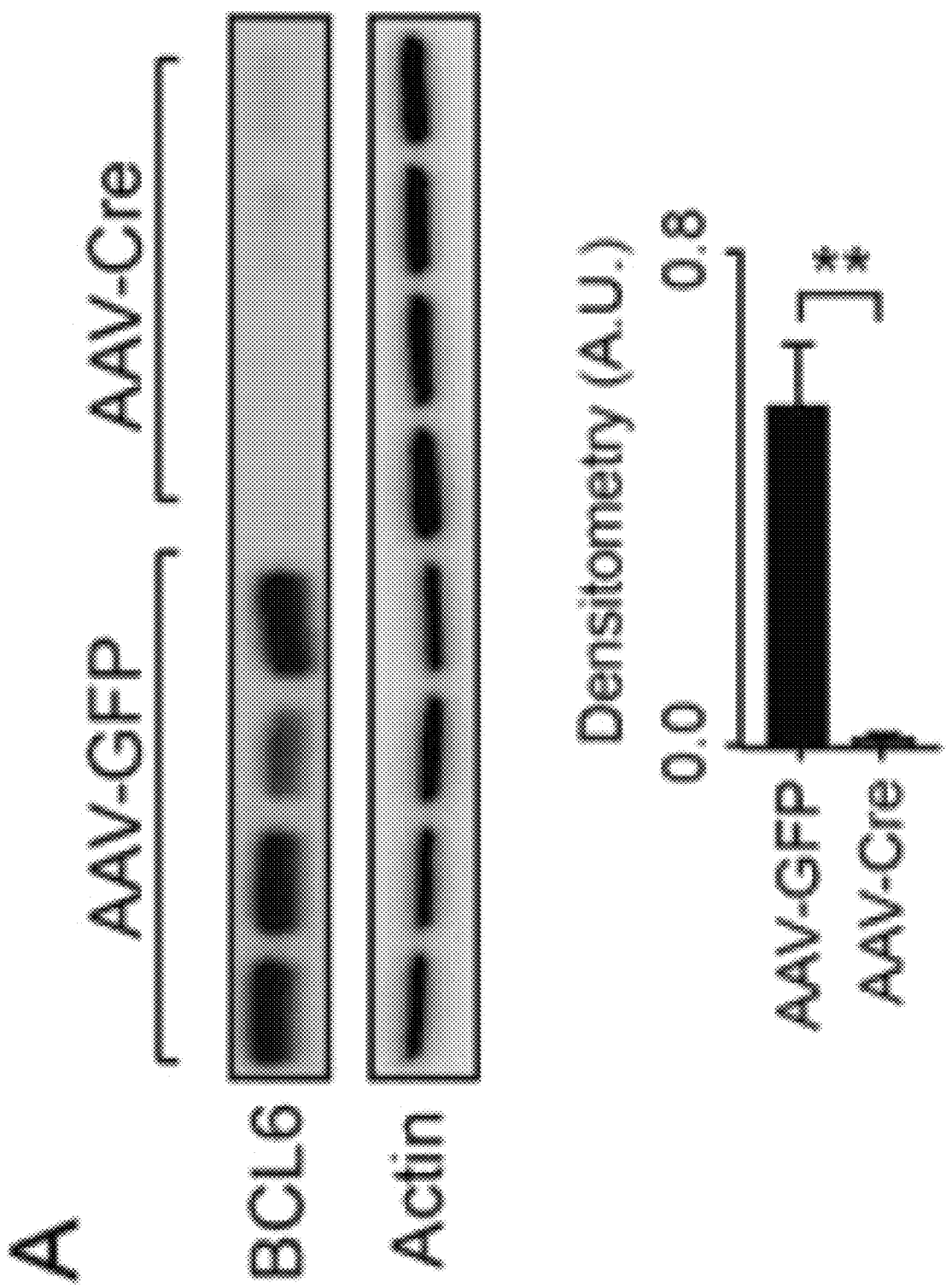
FIG. 6. Inducible deletion of hepatocyte Bcl6 in adult mice prevents weight gain and enhances glucose tolerance and glucose-stimulated insulin secretion. At 20 weeks of age, Bcl6$^{fl/fl}$ mice were infected with adeno-associated virus expressing GFP (AAV-GFP) or Cre (AAV-Cre) driven from the thyroid binding globulin promoter and analyzed to assess their metabolic responses. (A) Western blot showing BCL6 protein in AAV-GFP and AAV-Cre mice, revealing loss of BCL6 in AAV-Cre-infected mice. Densitometric analysis is shown normalized to actin (bottom). (B) Weight over time post-AAV injection expressed as % of initial body weight (BW) in AAV-GFP and AAV-Cre mice. N=9 per group. (C) Blood glucose levels during an intraperitoneal glucose tolerance test (GTT) after an overnight fast, intraperitoneal injection glucose dose=2 g/kg whole body weight. GTT was conducted 6 weeks post-AAV injection. N=9-10 per group. (D-F) Acute insulin secretion assays following intraperitoneal injection of 3 g/kg glucose, with (D) blood glucose, (E) serum insulin, and (F) serum C-peptide levels shown. A two-tailed Student's t-test assuming equal variance was used to compare means between two groups. Data are represented as mean±SEM. *p<0.05, p<0.01, *p<0.001.
Figure 6:
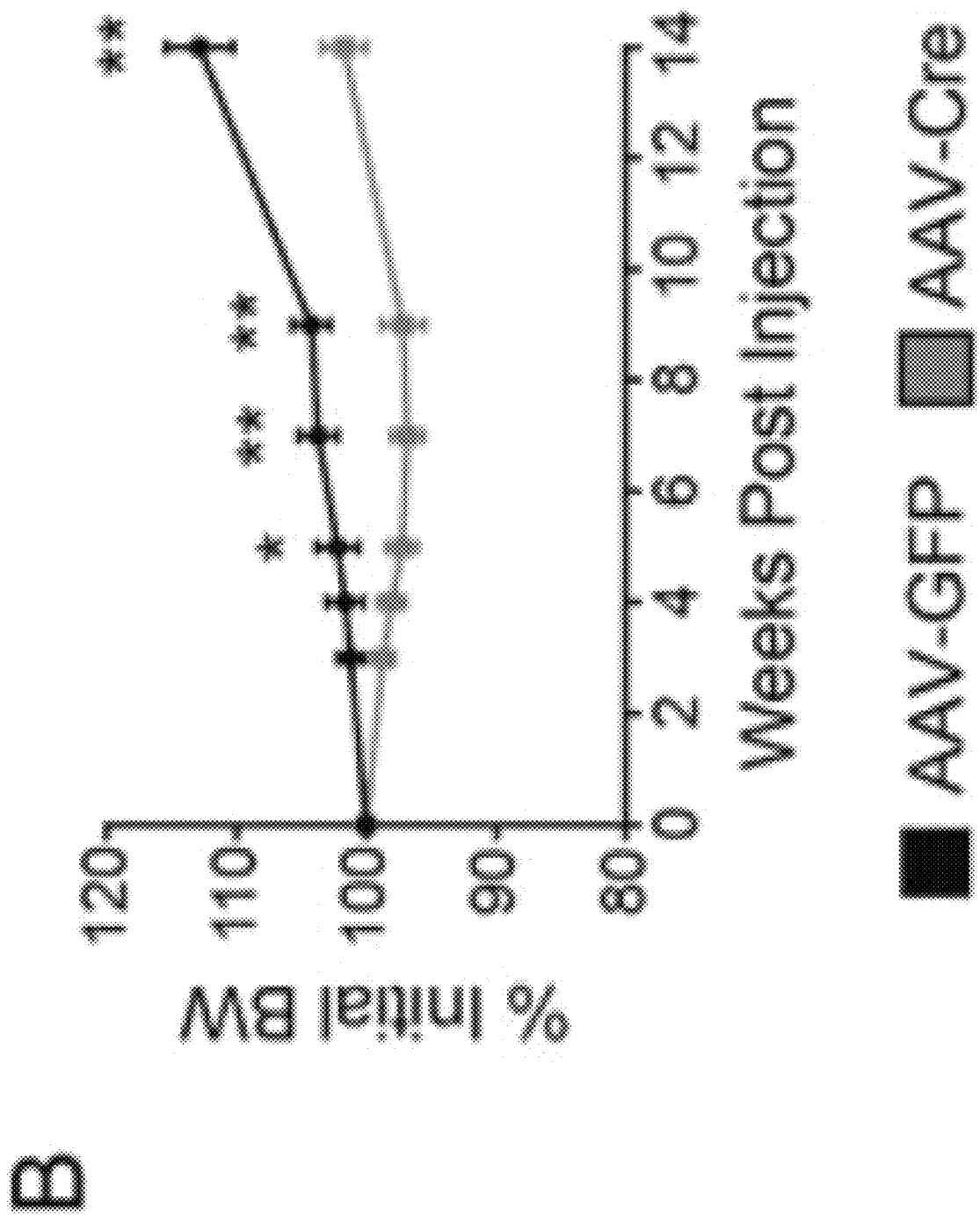
Figure 6:
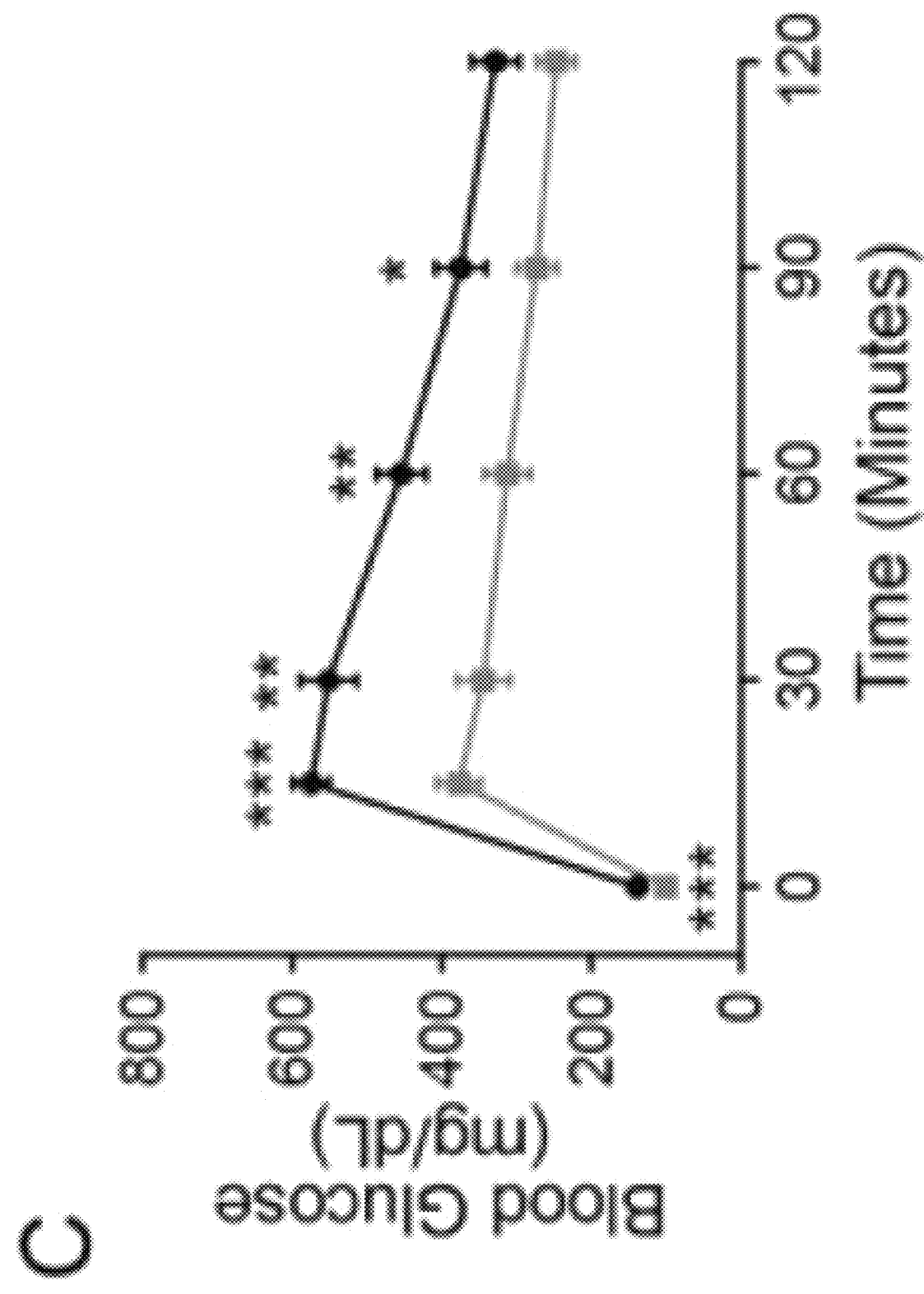
Figure 6:
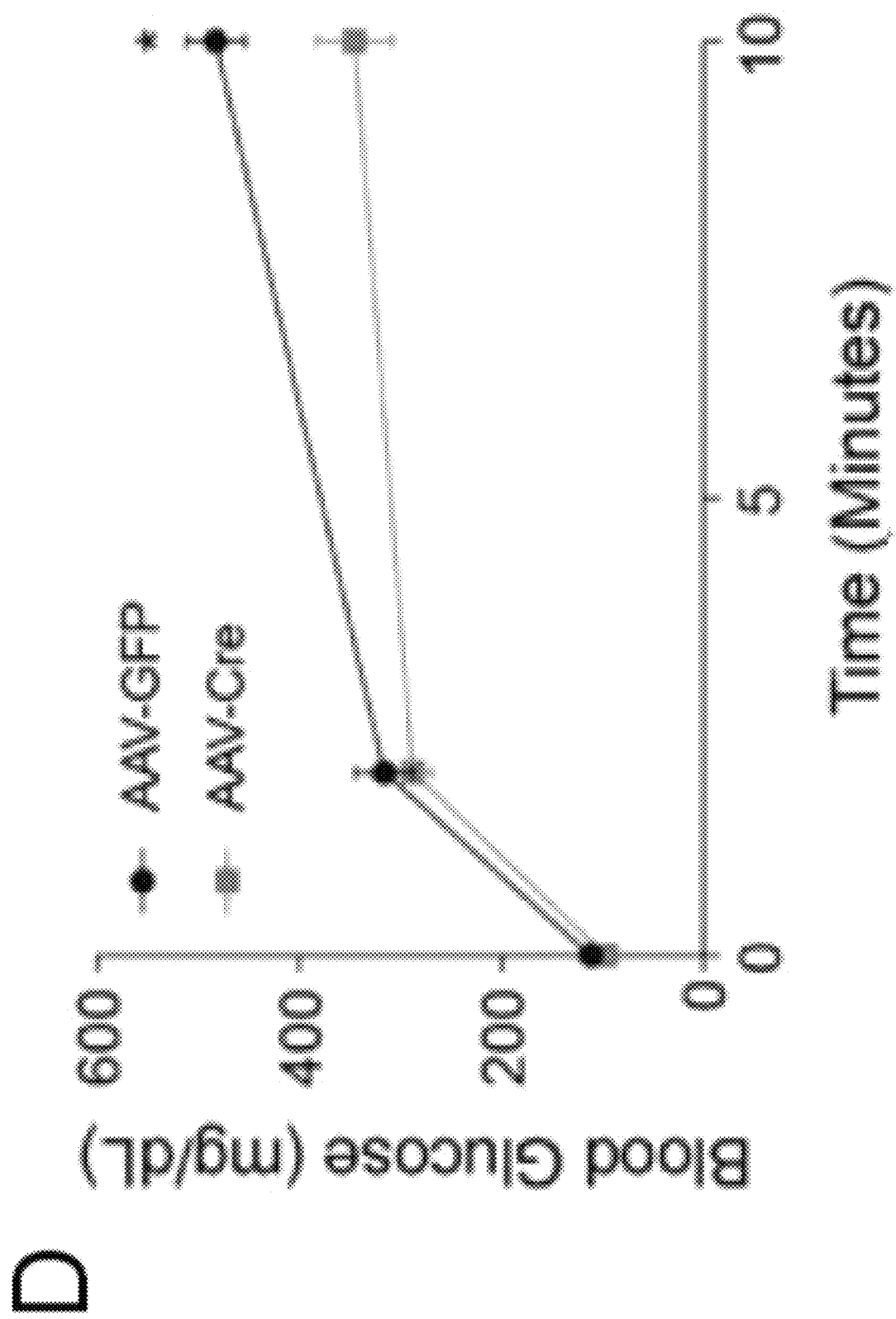
Figure 6:
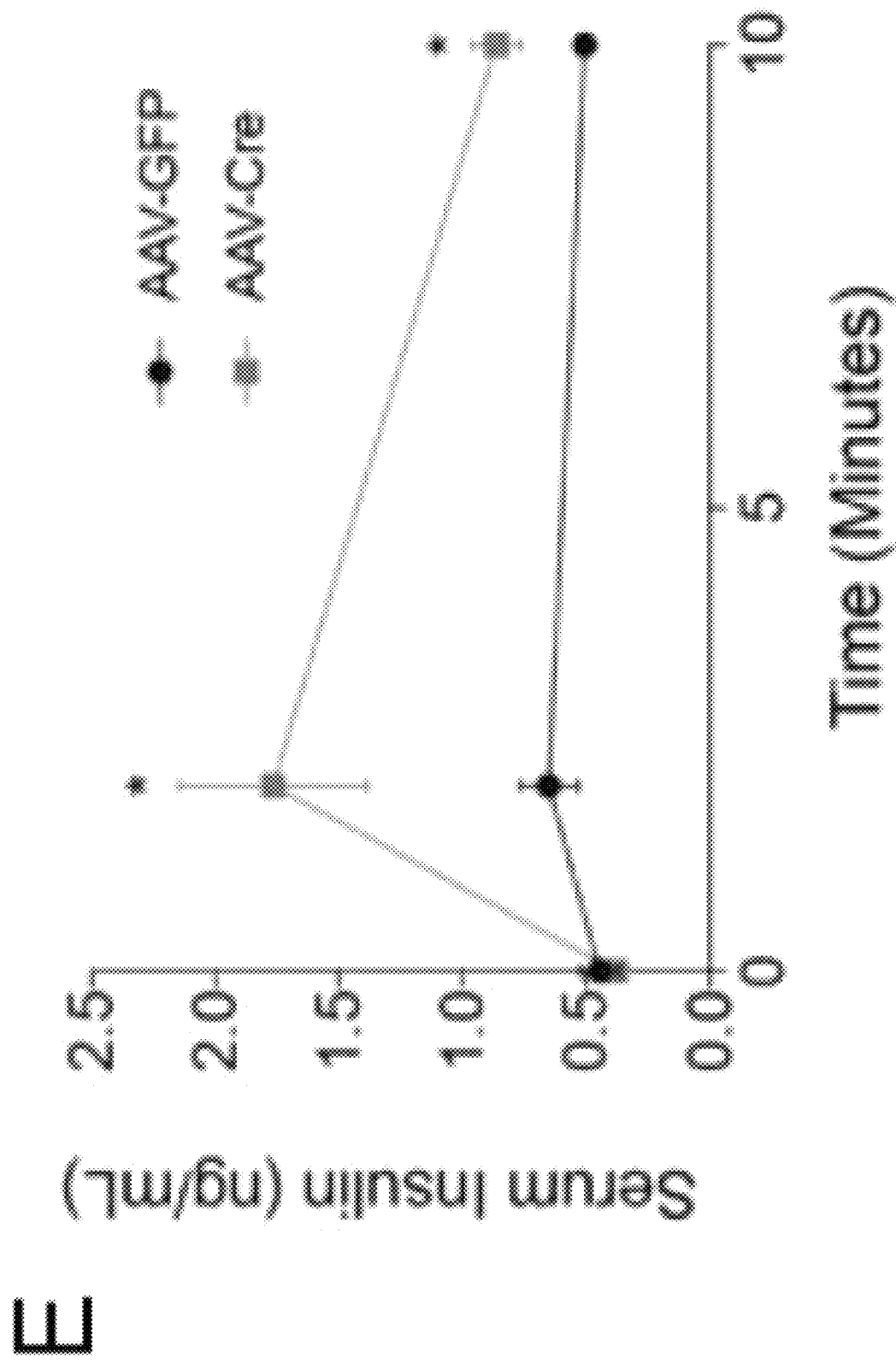
Figure 6:
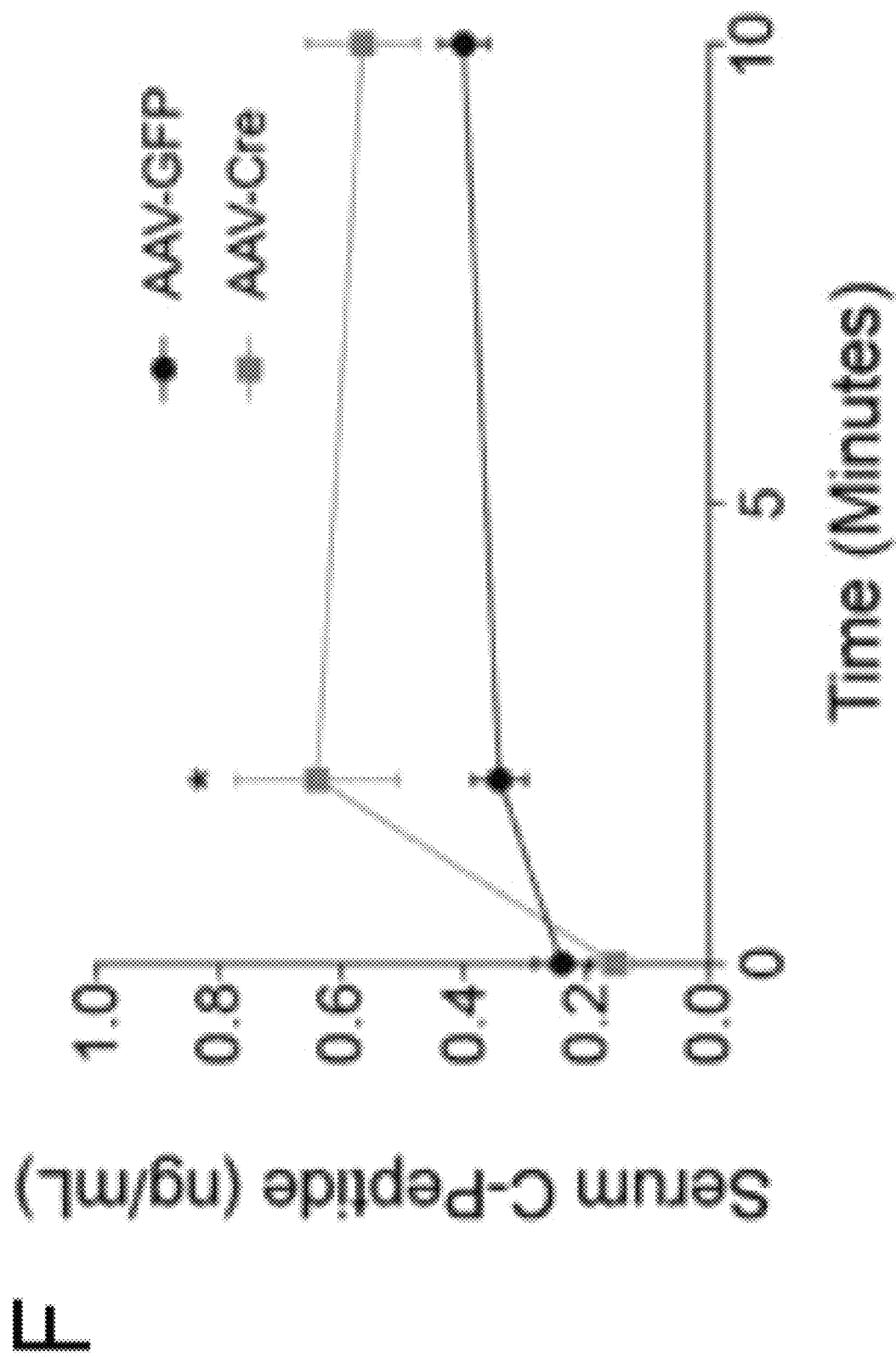

As illustrated in FIG. 6, adult mice that are inducibly ablated of hepatocyte Bcl6 have reduced weight gain, increased glucose tolerance, and increased glucose stimulated insulin secretion.

In summary, although BCL6 also regulates innate immune cell function [9], we have found that mice with macrophage-specific Bcl6 ablation exhibit normal glucose tolerance and are devoid of systemic inflammatory disease (Senagolage and Barish, unpublished), supporting our proposal that BCL6 targeting offers a novel avenue for NAFLD therapies.

Aim 1: To establish optimal dosing of BI-1136 for BCL6 degradation in liver

Rationale: BCL6 is a potent regulator of hepatic lipid metabolism and insulin sensitivity. Due to hepatic first pass effect, lower effective doses of BI-1136 may effectively target the liver while minimizing BCL6 degradation and potentially undesirable effects in other tissues.

Figure 7:
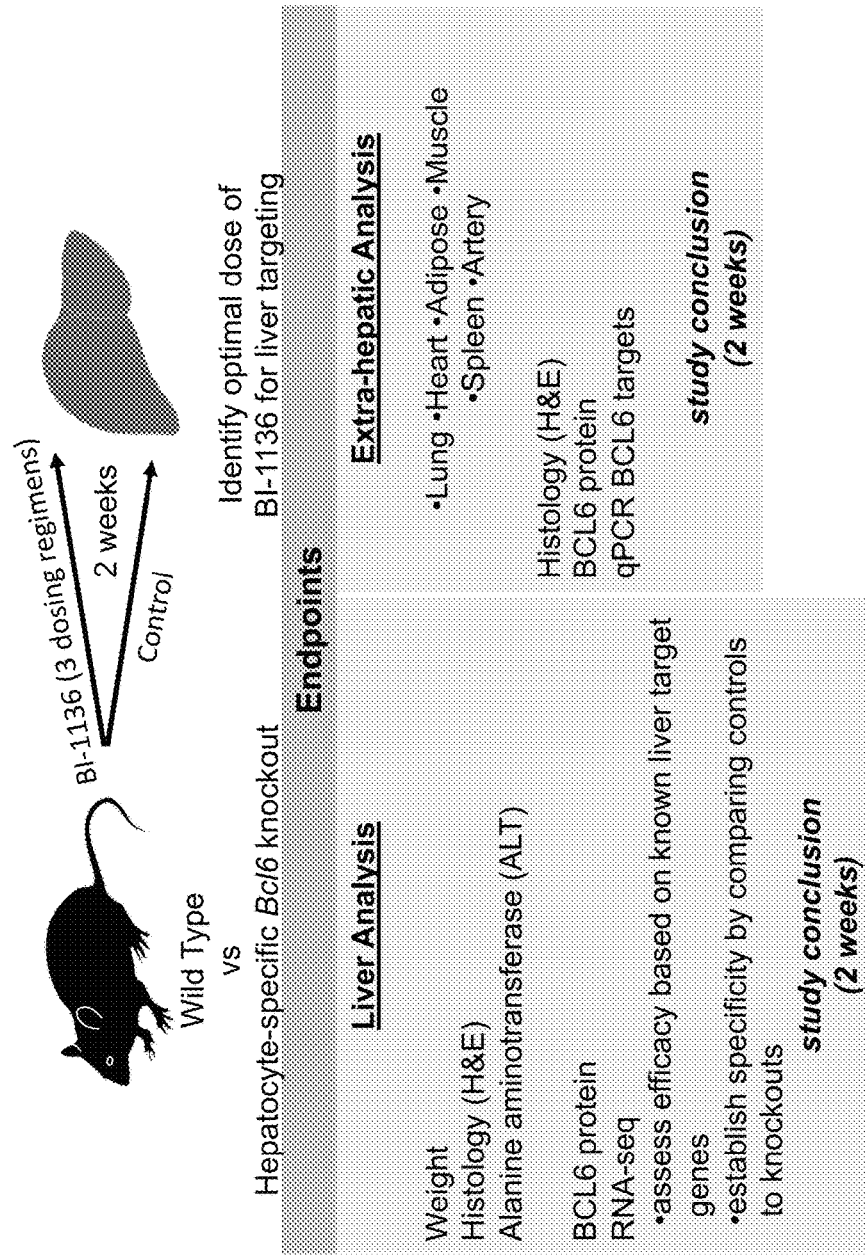
FIG. 7. Graphical representation of Aim 1 of the experimental plan of described in the Examples.

Approach: With feedback from Boehringer Ingelheim scientists, we will select up to 3 drug regimens to establish drug dosing efficacy (reduced BCL6 protein and associated changes in gene regulation), target specificity (Bcl6 genetic dependence for transcriptional effects), and tolerability (e.g. absence of pulmonary vasculitis and myocarditis as observed in Bcl6$^{-/-}$ mice [10], or hepatotoxicity) using wild type control (Bcl6$^{fl/fl}$) and hepatocyte-specific Bcl6 knockout mice. A graphical representation of the experimental plan is provided in FIG. 7.

Significance: We will identify an optimal BI-1136 treatment by establishing dosing that leads to efficient liver BCL6 degradation but minimizes degradation or toxicity in other tissues.

Alternative approaches: We have also developed a mouse line with Bcl6$^{fl/fl}$ crossed to CAGG-Cre-ER™ (Jackson Labs #004682) which results in widespread Bcl6 deletion following tamoxifen treatment. These animals lack Bcl6 in all liver cell types and could be used alternatively to establish Bcl6 genetic dependence for BI-1136.

Timeline: 2 months

Aim 2: To test the hypothesis that BCL6 degradation ameliorates type 2 diabetes mellitus and non-alcoholic steatohepatitis Rationale: Genetic deletion of Bcl6 in utero within adipocytes or hepatocytes results in insulin sensitivity and protection from steatosis. Thus, we hypothesize that targeting BCL6 genetically or pharmacologically may protect from the initiation and progression of NAFLD in rodent experimental models of the disease. FATZO (also known as MS-NASH) mice (Jackson Lab #030888) develop obesity spontaneously on a chow diet, display glucose intolerance and hyperinsulinemia by 6 weeks of age, and progress to overt diabetes with diminishing insulin levels as they age. Accordingly, they exhibit disease highly reminiscent of the metabolic syndrome in humans and respond to commonly used diabetes medications including thiazolidinediones, metformin, and GLP-1 agonists [11]. When subjected to Western diets supplemented with fructose, FATZO mice develop hepatic steatosis, inflammation, and fibrosis resembling human non-alcoholic fatty liver disease [12].

Figure 8:
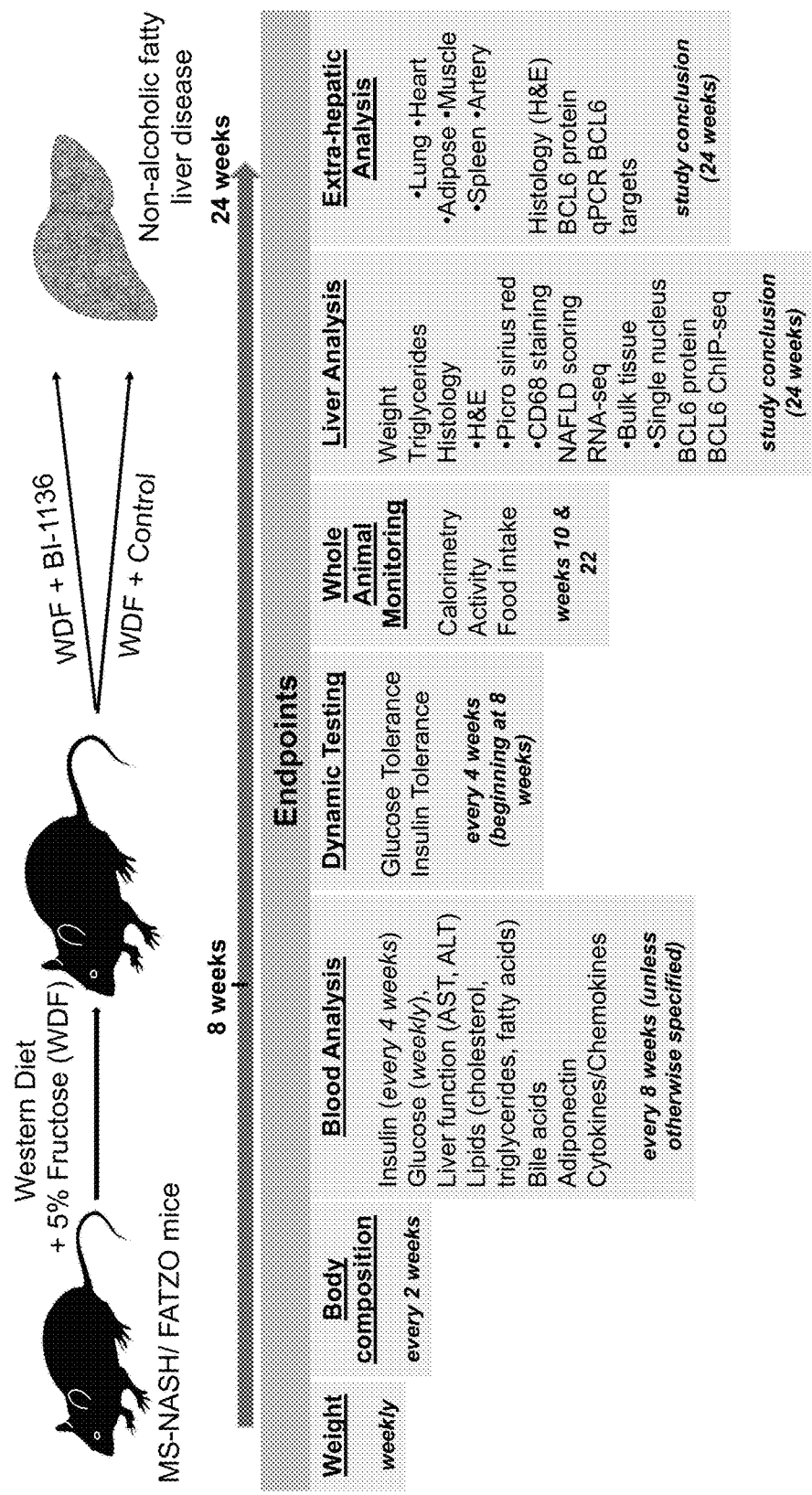
FIG. 8. Graphical representation of Aim 2 of the experimental plan of described in the Examples.

Approach: Using FATZO mice exposed to Western diet (Research Diets D12079B) and 5% fructose in drinking water, we will test the impact of the BCL6 degrader BI-1136 using a dosing regimen established from Aim 1. Analysis will include assessments of insulin resistance, inflammation, energy balance, non-alcoholic fatty liver disease, and gene regulation as detailed in FIG. 8. Liver pathology will be analyzed based upon a modified NAFLD Activity Score (NAS) validated for rodent models [13,14], and scored for fibrosis using established staging criteria [15]. Gene regulatory analysis will include BCL6 ChIP-sequencing in combination with bulk RNA-sequencing and single nucleus RNA-seq [16]. The latter will provide insight into the roles of varied liver cell types (hepatocytes, stellate cells, kupffer cells) in the observed therapeutic response to BI-1136.

Significance: These studies will comprehensively define the potential therapeutic efficacy of BI-1136 in NAFLD using a next-generation disease model that recapitulates the human metabolic syndrome and associated liver disease. Our analysis will bridge whole animal pathophysiology to BCL6 chromatin occupancy as well as bulk and single cell transcription to delineate molecular mechanisms for drug response.

Alternative approaches/future directions: Several other rodent models of NAFLD have been developed but have limitations that could limit their relevance to human disease. We have proposed the FATZO model as it recapitulates many key aspects of human NAFLD and type 2 diabetes mellitus. Alternative or additional test models could include our Bcl6 liver-specific or adipocyte-specific knockout mice and their respective controls which are in the C57Bl/6 background. These can also develop steatohepatitis but require high fat/high fructose diets supplemented with supraphysiologiocal levels of dietary cholesterol (2%) [17]. Despite this limitation, these models would allow us to further demonstrate Bcl6 genetic dependence and tissue contributions for BI-1136 effects in NAFLD-like disease.

Timeline: 10 months

References

1. Dyson J K, Anstee Q M, McPherson S. Non-alcoholic fatty liver disease: a practical approach to treatment. Frontline Gastroenterol. 2014; 5(4):277-86. Epub 2014/10/07. doi: 10.1136/flgastro-2013-100404. PubMed PMID: 25285192; PMCID: PMC4173737.
2. Matteoni C A, Younossi Z M, Gramlich T, Boparai N, Liu Y C, McCullough A J. Nonalcoholic fatty liver disease: a spectrum of clinical and pathological severity. Gastroenterology. 1999; 116(6):1413-9. Epub 1999/05/29. PubMed PMID: 10348825.
3. Ekstedt M, Franzen L E, Mathiesen U L, Thorelius L, Holmqvist M, Bodemar G, Kechagias S. Long-term follow-up of patients with NAFLD and elevated liver enzymes. Hepatology. 2006; 44(4):865-73. Epub 2006/09/29. doi: 10.1002/hep.21327. PubMed PMID: 17006923.
4. Younossi Z M, Blissett D, Blissett R, Henry L, Stepanova M, Younossi Y, Racila A, Hunt S, Beckerman R. The economic and clinical burden of nonalcoholic fatty liver disease in the United States and Europe. Hepatology. 2016; 64(5):1577-86. Epub 2016/10/22. doi: 10.1002/hep.28785. PubMed PMID: 27543837.
5. Roglic G, World Health Organization. Global report on diabetes. Geneva, Switzerland: World Health Organization; 2016. 86 pages p.
6. American Diabetes A. Economic Costs of Diabetes in the U.S. in 2017. Diabetes Care. 2018; 41(5):917-28. Epub 2018/03/24. doi: 10.2337/dci18-0007. PubMed PMID: 29567642; PMCID: PMC5911784.
7. Senagolage M D, Sommars M A, Ramachandran K, Futtner C R, Omura Y, Allred A L, Wang J, Yang C, Procissi D, Evans R M, Han X, Bederman I R, Barish G D. Loss of Transcriptional Repression by BCL6 Confers Insulin Sensitivity in the Setting of Obesity. Cell Rep. 2018; 2 5(12): 3283-98 e6. Epub 2018/12/20. doi: 10.1016/j.celrep.2018.11.074. PubMed PMID: 30566857; PMCID: PMC6377366.
8. Sommars M A, Ramachandran K, Senagolage M D, Futtner C R, Germain D M, Allred A L, Omura Y, Bederman I R, Barish G D. Dynamic repression by BCL6 controls the genome-wide liver response to fasting and steatosis. Elife. 2019; 8. Epub 2019/04/16. doi: 10.7554/eLife.43922. PubMed PMID: 30983568; PMCID: PMC6464608.
9. Barish G D, Yu R T, Karunasiri M, Ocampo C B, Dixon J, Benner C, Dent A L, Tangirala R K, Evans R M. Bcl-6 and NF-kappaB cistromes mediate opposing regulation of the innate immune response. Genes Dev. 2010; 24(24):2760-5. Epub 2010/11/26. doi: 10.1101/gad.1998010. PubMed PMID: 21106671; PMCID: PMC3003193.
10. Dent A L, Shaffer A L, Yu X, Allman D, Staudt L M. Control of inflammation, cytokine expression, and germinal center formation by BCL-6. Science. 1997; 276(5312):589-92. Epub 1997/04/25. doi: 10.1126/science.276.5312.589. PubMed PMID: 9110977.
11. Peterson R G, Jackson C V, Zimmerman K M, Alsina-Fernandez J, Michael M D, Emmerson P J, Coskun T. Glucose dysregulation and response to common antidiabetic agents in the FATZO/Pco mouse. PloS one. 2017; 12(6):e0179856. Epub 2017/06/24. doi: 10.1371/journal.pone.0179856. PubMed PMID: 28640857; PMCID: PMC5480999.
12. Sun G, Jackson C V, Zimmerman K, Zhang L K, Finnearty C M, Sandusky G E, Zhang G, Peterson R G, Wang Y J. The FATZO mouse, a next generation model of type 2 diabetes, develops NAFLD and NASH when fed a Western diet supplemented with fructose. BMC Gastroenterol. 2019; 19(1):41. Epub 2019/03/20. doi: 10.1186/s12876-019-0958-4. PubMed PMID: 30885145; PMCID: PMC6421686.

13. Kleiner D E, Brunt E M, Van Natta M, Behling C, Contos M J, Cummings O W, Ferrell L D, Liu Y C, Torbenson M S, Unalp-Arida A, Yeh M, McCullough A J, Sanyal A J, Nonalcoholic Steatohepatitis Clinical Research N. Design and validation of a histological scoring system for nonalcoholic fatty liver disease. Hepatology. 2005; 41(6): 1313-21. Epub 2005/05/26. doi: 10.1002/hep.20701. PubMed PMID: 15915461.

14. Liang W, Menke A L, Driessen A, Koek G H, Lindeman J H, Stoop R, Havekes L M, Kleemann R, van den Hoek A M. Establishment of a general NAFLD scoring system for rodent models and comparison to human liver pathology. PloS one. 2014; 9(12):e115922. Epub 2014/12/24. doi: 10.1371/journal.pone.0115922. PubMed PMID: 25535951; PMCID: PMC4275274.

15. Brunt E M, Janney C G, Di Bisceglie A M, Neuschwander-Tetri B A, Bacon B R. Nonalcoholic steatohepatitis: a proposal for grading and staging the histological lesions. Am J Gastroenterol. 1999; 94(9):2467-74. Epub 1999/09/14. doi: 10.1111/j.1572-0241.1999.01377.x. PubMed PMID: 10484010.

16. Grindberg R V, Yee-Greenbaum J L, McConnell M J, Novotny M, O'Shaughnessy A L, Lambert G M, Arauzo-Bravo M J, Lee J, Fishman M, Robbins G E, Lin X, Venepally P, Badger J H, Galbraith D W, Gage F H, Lasken R S. RNA-sequencing from single nuclei. Proc Natl Acad Sci USA. 2013; 110(49):19802-7. Epub 2013/11/20. doi: 10.1073/pnas.1319700110. PubMed PMID: 24248345; PMCID: PMC3856806.

Farrell G, Schattenberg J M, Leclercq I, Yeh M M, Goldin R, Teoh N, Schuppan D. Mouse Models of Nonalcoholic Steatohepatitis: Toward Optimization of Their Relevance to Human Nonalcoholic Steatohepatitis. Hepatology. 2019; 69(5):2241-57. Epub 2018/10/30. doi: 10.1002/hep.30333. PubMed PMID: 30372785.

Example 2

Figure 9:
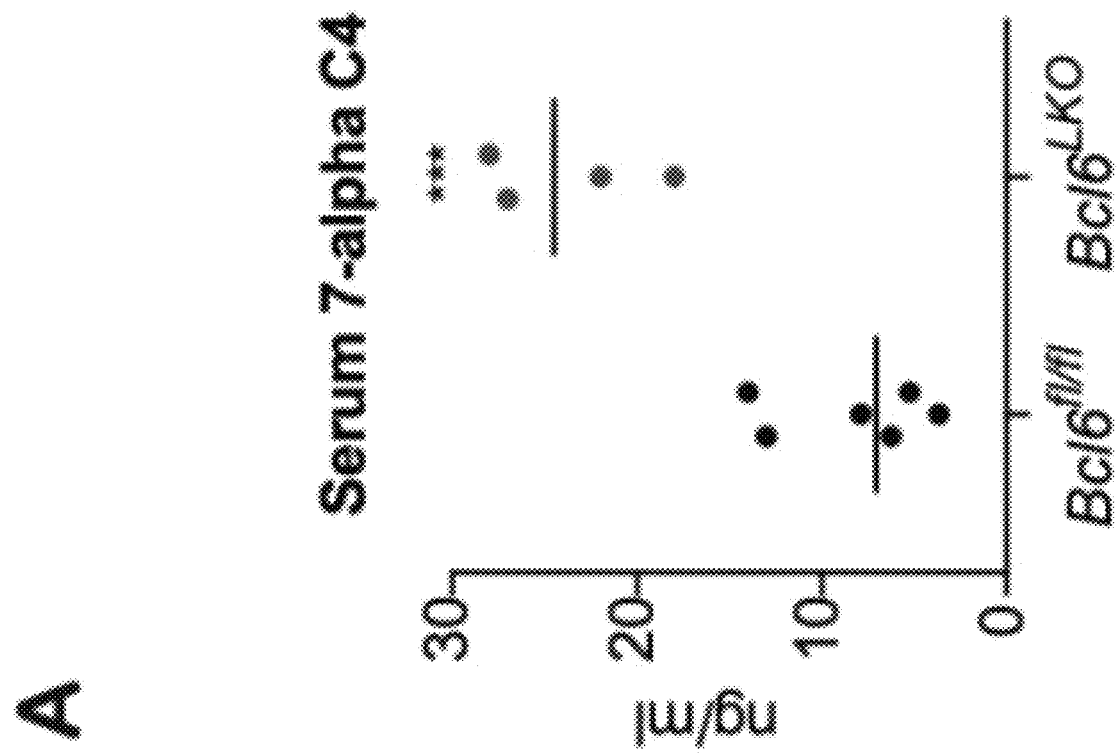
FIG. 9. (A) Mice lacking Bcl6 in hepatocytes (Bcl6$^{LKO}$) have elevated serum levels of the bile acid synthetic intermediate 7-alpha C4 compared to wild type control (Bcl6$^{fl/fl}$) animals. (B) Bcl6$^{LKO}$ mice have elevated serum levels of total bile acids and various bile acid subspecies including cholic acid, deoxycholic acid, and ursodeoxycholic acid compared to Bcl6$^{fl/fl}$ controls. Data is shown for male mice, n=10/group. Quantification was performed using LC-MS/MS with the Biocrates Bile Acids kit. (C) Quantitative PCR interrogation of preproglucagon expression in fed and fasted mice in brown adipose tissue, duodenum, ileum, and colon in Bcl6$^{fl/fl}$ and Bcl6$^{LKO}$ mice, N=5 mice/group. (D,E) Simultaneous assay of oral glucose tolerance (D) and GLP-1 protein levels (E) in Bcl6$^{fl/fl}$ and Bcl6$^{LKO}$ male mice as determined by enzyme-linked immunosorbent assay. 45 minutes prior to an oral glucose bolus of 2 mg/kg, all mice were treated with the dipeptidyl peptidase 4 inhibitor Saxagliptin (10 mg/kg) to prevent degradation of GLP-1, N=4 mice/group. For all subpanels, *p-value<0.05, p-value<0.01, *p-value<0.001.
Figure 9:
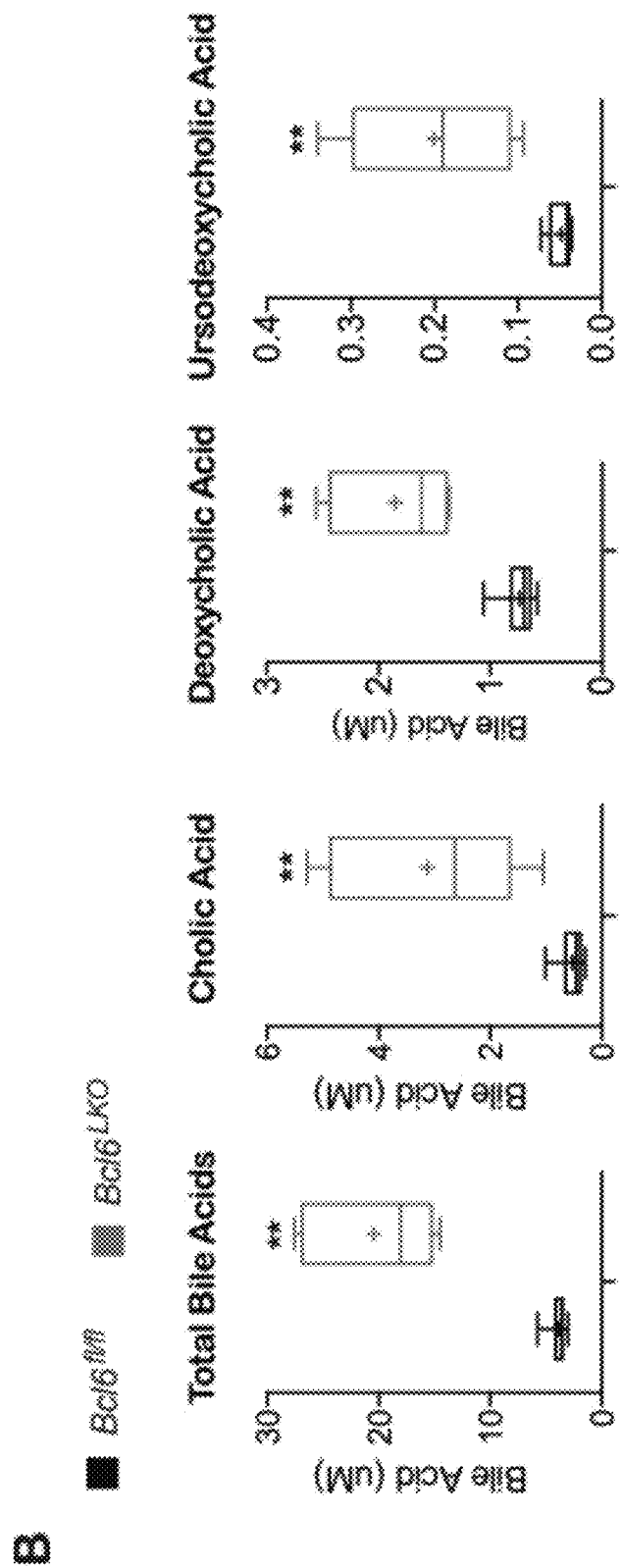
Figure 9:
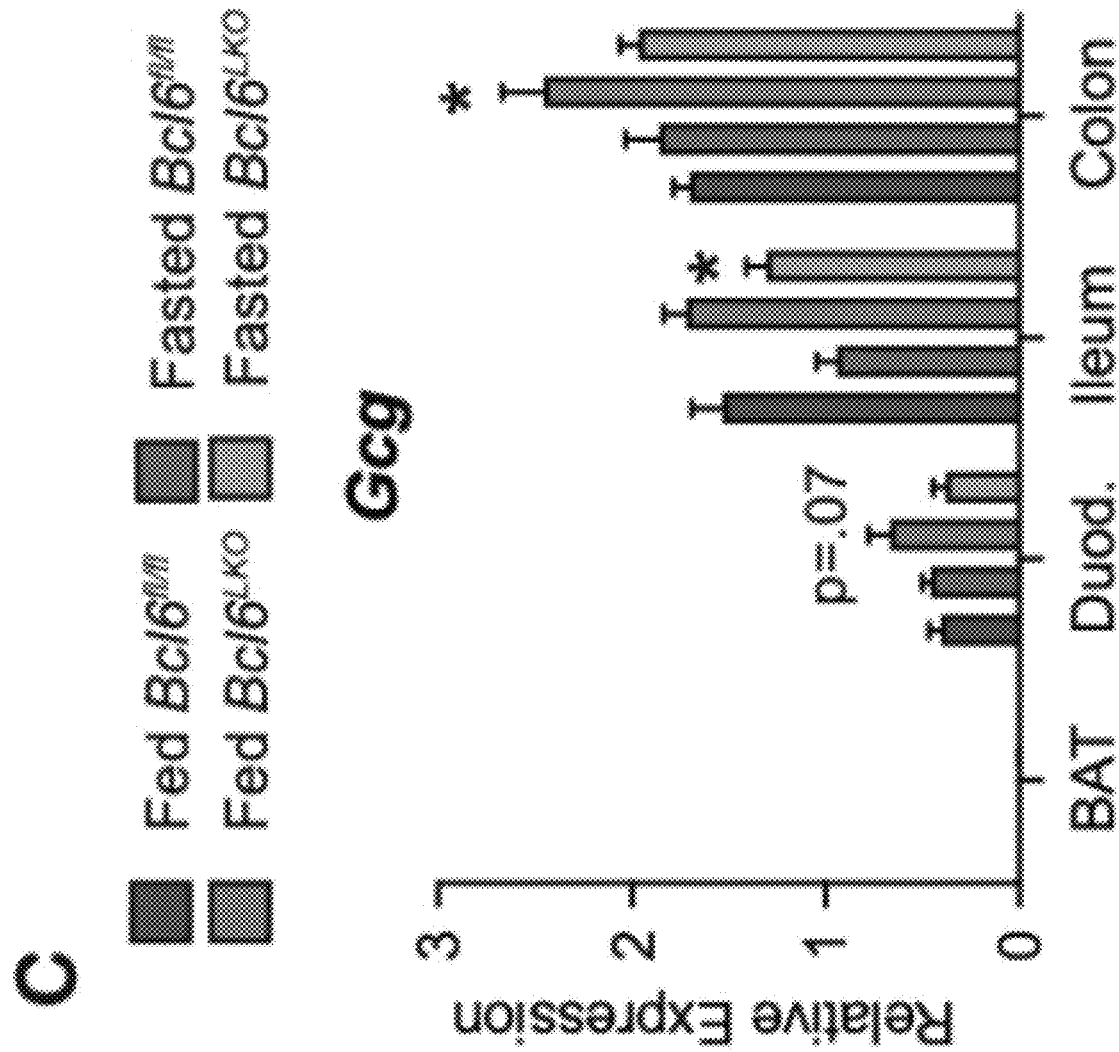
Figure 9:
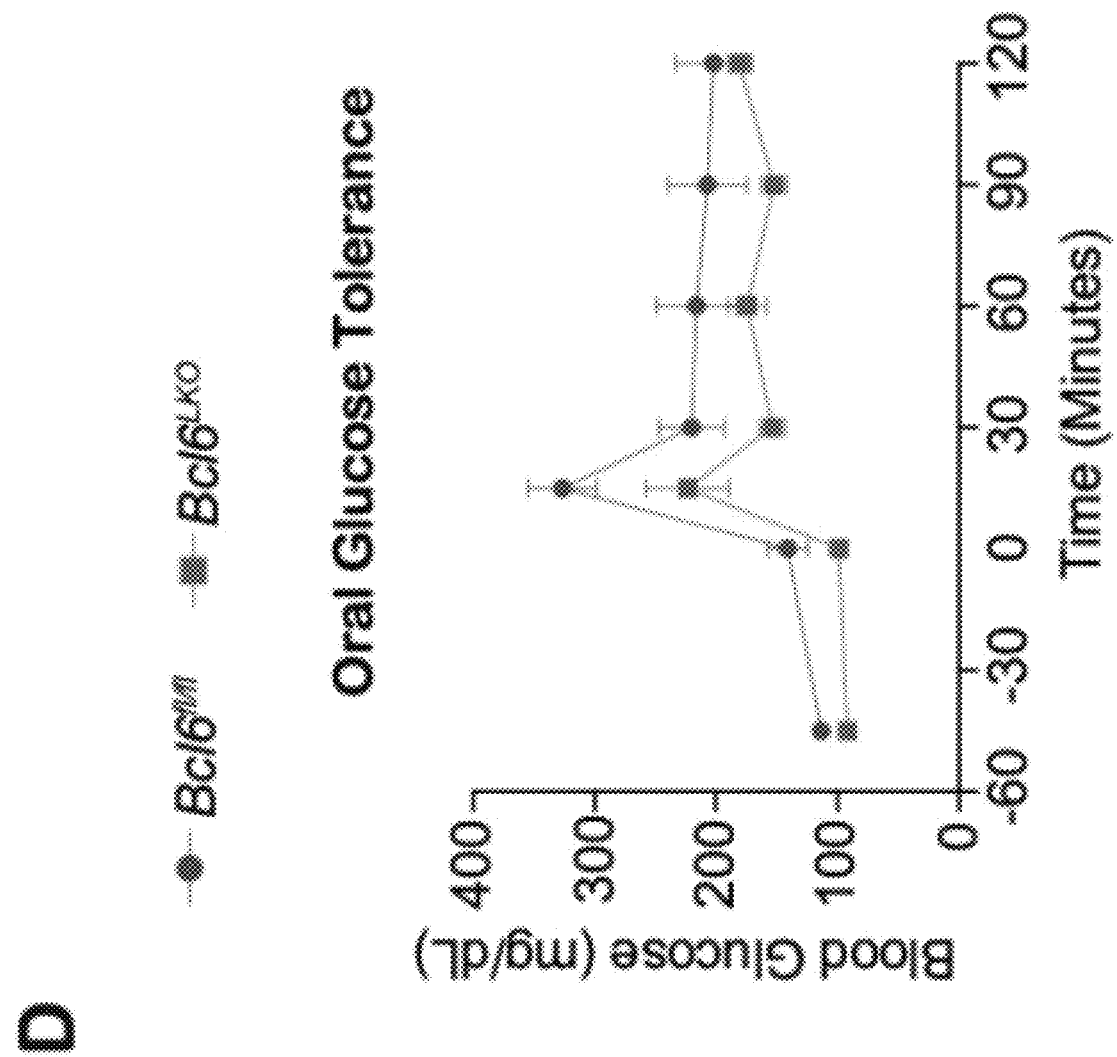
Figure 9:
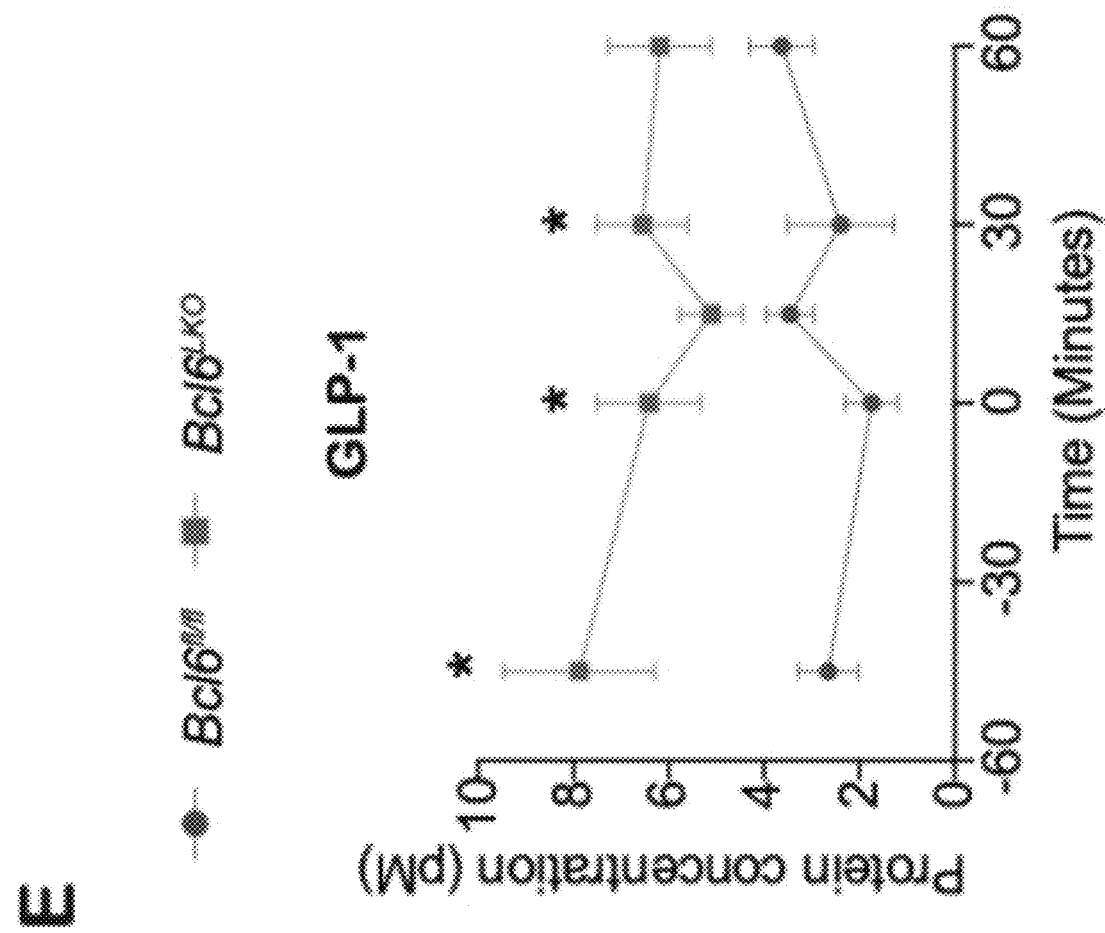

Title—Genetic Ablation of Bcl6 in the Liver Results in a Marked Increased in Bile Acid Synthesis We have discovered that genetic ablation of Bcl6 in the liver results in a marked increase in bile acid synthesis (FIG. 9A) leading to ~4-fold increased levels of serum bile acids (FIG. 9B, left). Among these elevated bile acids are multiple subspecies implicated in signaling through G protein-coupled bile acid receptor 1 (GPBAR1, also known as Takeda G-protein receptor 5) and Farnesoid-X-Receptor (FXR) including cholic acid, deoxycholic acid, and ursodeoxycholic acid (FIG. 9B, right). Elevations in the levels of these naturally occurring bile acid receptor ligands are anticipated to improve insulin sensitivity and increase energy expenditure [1-3]. Additionally, activation of GPBAR1 signaling has been implicated in protection against steatosis and obesity as well as upregulation of the incretin hormone glucagon-like peptide-1 (GLP-1), leading to enhanced insulin secretion and glucose tolerance [4]. In line with this, we have discovered that loss of Bcl6 in liver results in increased RNA expression of the preproglucagon (Gcg) gene in various sections of the intestine (FIG. 9C), which is post-translationally processed to become GLP-1. Moreover, both before and over the course of an oral glucose tolerance test, serum levels of GLP-1 protein are significantly elevated in mice lacking Bcl6 in liver (FIGS. 9D-E). In summary, the signaling effects of bile acids and associated induction of GLP-1 are predicted to contribute to improved energy homeostasis, protection from non-alcoholic fatty liver disease, and enhanced glucose homeostasis with genetic or pharmacologic inhibition of BCL6 in hepatocytes [5].

REFERENCES

1. Watanabe, M., et al., Bile acids induce energy expenditure by promoting intracellular thyroid hormone activation. Nature, 2006. 439(7075): p. 484-9.

2. Watanabe, M., et al., Bile acids lower triglyceride levels via a pathway involving FXR, SHP, and SREBP-lc. J Clin Invest, 2004. 113(10): p. 1408-18.

3. Ozcan, U., et al., Chemical chaperones reduce ER stress and restore glucose homeostasis in a mouse model of type 2 diabetes. Science, 2006. 313(5790): p. 1137-40.

4. Thomas, C., et al., TGR5-mediated bile acid sensing controls glucose homeostasis. Cell Metab, 2009. 10(3): p. 167-77.

5. Chiang, J. Y. L. and J. M. Ferrell, Bile acid receptors FXR and TGR5 signaling in fatty liver diseases and therapy. Am J Physiol Gastrointest Liver Physiol, 2020. 318(3): p. G554-G573.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating non-alcoholic fatty liver disease in a subject in need thereof, the method comprising administering to the subject a therapeutic agent that inhibits the expression of B cell lymphoma protein 6 (BCL6).

2. The method of claim 1, comprising inhibiting expression of BCL6 in adipocytes.

3. The method of claim 1, comprising inhibiting expression of BCL6 in hepatocytes.

4. The method of claim 1, wherein the method promotes insulin sensitivity.

5. The method of claim 1, wherein the method prevents hepatic steatosis.

6. The method of claim 1, wherein the method enhances glucose tolerance.

7. The method of claim 1, wherein the method enhances glucose-stimulated insulin secretion.

8. The method of claim 1, wherein the method prevents weight gain.

\* \* \* \* \*

UNITED STATES PATENT AND TRADEMARK OFFICE
CERTIFICATE OF CORRECTION

PATENT NO.         : 11,439,635 B2
APPLICATION NO.    : 16/943519
DATED              : September 13, 2022
INVENTOR(S)        : Grant D. Barish et al.

Page 1 of 1

It is certified that error appears in the above-identified patent and that said Letters Patent is hereby corrected as shown below:

In the Specification

Column 2, Line 60, "Bcl6$^{iAKO}$" should be --Bcl6$^{LKO}$--.

Column 8, Line 5, "IC$_{SO}$" should be --IC$_{50}$--.

Column 22, Line 20, "TGRS-mediated" should be --TGR5-mediated--.

Signed and Sealed this
Twenty-third Day of May, 2023

Katherine Kelly Vidal
*Director of the United States Patent and Trademark Office*